United States Patent
Johnson et al.

(10) Patent No.: US 10,964,426 B2
(45) Date of Patent: Mar. 30, 2021

(54) METHODS AND SYSTEMS TO SENSE SITUATIONAL AWARENESS WITH A DUAL DOPPLER AND CONTROL FOR OPTIMIZED OPERATIONS

(71) Applicant: General Electric Company, Schenectady, NY (US)

(72) Inventors: Christopher Donald Johnson, Niskayuna, NY (US); Brandon Stephen Good, Niskayuna, NY (US); Andrew Phelps Day, Newtown, PA (US); David S. Toledano, Niskayuna, NY (US); Yang Zhao, Niskayuna, NY (US); Jeffrey Richardson Terry, Lewisville, TX (US)

(73) Assignee: General Electric Company, Schenectady, NY (US)

( * ) Notice: Subject to any disclaimer, the term of this patent is extended or adjusted under 35 U.S.C. 154(b) by 1109 days.

(21) Appl. No.: 14/885,169

(22) Filed: Oct. 16, 2015

(65) Prior Publication Data
US 2017/0109481 A1 Apr. 20, 2017

(51) Int. Cl.
*G16H 40/20* (2018.01)
*G06F 19/00* (2018.01)

(52) U.S. Cl.
CPC .............. *G16H 40/20* (2018.01); *G06F 19/00* (2013.01)

(58) Field of Classification Search
CPC .......... G08B 19/00; H04N 7/18; G16H 40/20; G06Q 50/00; G06Q 10/00; G01S 13/88;
(Continued)

(56) References Cited

U.S. PATENT DOCUMENTS 7,756,723 B2 * 7/2010 Rosow .................. G06Q 10/02
705/2
8,068,051 B1 * 11/2011 Osterweil ............... G01S 7/006
342/28
(Continued)

FOREIGN PATENT DOCUMENTS

CA 2160352 A1 * 10/1994 ........... A61B 5/0507
JP 2003050276 A * 2/2003

OTHER PUBLICATIONS

Wang, Yazhou, "UWB Pulse Radar for Human Imaging and Doppler Detection Applications." PhD diss., University of Tennessee, 2012. (Year: 2012).*
(Continued)

*Primary Examiner* — Fonya M Long
*Assistant Examiner* — Alaaeldin M Elshaer

(57) ABSTRACT

Certain examples provide systems and methods to monitor and control hospital operational systems based on occupancy data and medical orders. An example healthcare workflow management and reasoning system includes a workflow engine including a first particularly programmed processor to monitor one or more medical orders from one or more hospital information systems to identify a condition indicating that a first patient in a first room is ready for a clinical activity such as discharge. The example healthcare workflow management and reasoning system includes a sensing component including a second processor to gather occupancy data regarding the first patient in the first room and transmit the occupancy data to the workflow engine. The example workflow engine controls one or more hospital operational systems to trigger cleaning of the first room, lighting settings for the first room, and transportation of a second patient to the first room based on occupancy data from the sensing component.

15 Claims, 21 Drawing Sheets

(58) Field of Classification Search
CPC .......... G01S 13/62; G06F 19/00; G06F 3/048; G06F 7/05
USPC .................................. 705/2, 3, 600; 715/771
See application file for complete search history.

(56) References Cited

U.S. PATENT DOCUMENTS

| | | | | |
|---|---|---|---|---|
| 8,635,088 | B2* | 1/2014 | Yelton | G06Q 10/02 705/3 |
| 8,732,573 | B2* | 5/2014 | Nacey | G06F 17/246 715/251 |
| 8,930,215 | B2* | 1/2015 | Goldberg | G06Q 50/22 705/2 |
| 9,122,373 | B1* | 9/2015 | Nacey | G06F 3/0484 |
| 9,495,569 | B2* | 11/2016 | Theurer | G06K 7/10366 |
| 2009/0089092 | A1* | 4/2009 | Johnson | G06Q 10/06 705/2 |
| 2011/0208541 | A1* | 8/2011 | Wilson | A61G 7/018 705/3 |
| 2012/0154582 | A1* | 6/2012 | Johnson | G06F 19/321 348/143 |
| 2012/0323090 | A1* | 12/2012 | Bechtel | A61B 5/6889 600/306 |
| 2013/0024029 | A1* | 1/2013 | Tran | A61B 5/1113 700/278 |
| 2013/0085609 | A1* | 4/2013 | Barker | G05B 15/02 700/276 |
| 2015/0081326 | A1* | 3/2015 | Krishnapuram | G06Q 10/06311 705/2 |
| 2015/0212205 | A1* | 7/2015 | Shpater | G01S 13/38 342/28 |

OTHER PUBLICATIONS

C. Li, V. M. Lubecke, O. Boric-Lubecke and J. Lin, "A Review on Recent Advances in Doppler Radar Sensors for Noncontact Healthcare Monitoring," in IEEE Transactions on Microwave Theory and Techniques, vol. 61, No. 5, pp. 2046-2060, May 2013 (Year: 2013).*

D. Kellner, M. Barjenbruch, J. Klappstein, J. Dickmann and K. Dietmayer, "Instantaneous full-motion estimation of arbitrary objects using dual Doppler radar," 2014 IEEE Intelligent Vehicles Symposium Proceedings, Dearborn, MI, 2014, pp. 324-329, doi: 10.1109/IVS.2014.6856449. (Year: 2014).*

V. P. Tran and A. A. Al-Jumaily, "Non-contact dual pulse Doppler system based respiratory and heart rates estimation for CHF patients," 2015 37th Annual International Conference of the IEEE Engineering in Medicine and Biology Society (EMBC), Milan, 2015, pp. 4202-4205, doi: 10.1109/EMBC.2015.7319321. (Year: 2015).*

* cited by examiner

|  | A 815 | B 820 | C 825 |
|---|---|---|---|
| 850 — Switched / Fluorescent 854 | 120 VAC | 120 VAC | 120 VAC |
| 851 — Switched with Dimmer / LED 855 | 0 → 120 VAC  860 | 0 → 120 VAC | N/A |
| 852 — D Controller / Fluorescent | 120 on 0 off | 120 on 0 off | 120 VAC |
| | 0 → 120 VAC  861 | 0 → 120 VAC | 120 VAC |
| 853 — LAN / N/A | LED  862 | N/A | LAN Power |

FIG. 11

METHODS AND SYSTEMS TO SENSE SITUATIONAL AWARENESS WITH A DUAL DOPPLER AND CONTROL FOR OPTIMIZED OPERATIONS

BACKGROUND

The statements in this section merely provide background information related to the disclosure and may not constitute prior art.

Many operational environments face constant pressures on available capacity, and, if decision support tools are not available to help automatically control and/or otherwise manage throughput, the result can be long waiting times and inefficient performance such as inefficient resource utilization. In a hospital, inpatient beds often pose a capacity constraint which limits throughput of an emergency department, surgical suites and other potential sources of patient admissions.

Most hospitals employ bed management processes or systems which may report on patients waiting for admission as well as current inpatients who are scheduled for discharge. However, there is typically a large amount of manual intervention required by hospital staff in order to ensure that these systems reflect the current occupancy or availability status of specific hospital beds. Conditionally critical path workflows, such as the assignment of beds and activation of cleaning and transfer resources to serve hospital stakeholders are typically intensively manual processes and are informed by local, not hospital wide, dynamical flows through time. Therefore, a lack of information and poor awareness to actual patient status (such as whether a particular inpatient has actually discharged from the hospital and finally departed their room) lengthens the timespan required for such operational activities and ties up scarce bed capacity in dynamically constrained operations.

Discharge and departure of a patient typically requires that a discharge order be written (or noted electronically), that the patient has completed any other outstanding orders (such as for additional in-house tests, scans or therapies). After these prerequisites are completed, the patient must physically vacate their bed and room, which may take an indeterminate amount of time during which the bed is not available for use by a new patient. Following the final vacating of the bed and room, cleaning staff must be activated to clean the room and transfer staff must then be summoned to transfer a new admission to this bed. These follow-on activities cannot proceed until the bed's current occupant has been confirmed as discharged and departed, and are typically activated manually by hospital staff.

Nurses and unit administrators may report discharge information to the bed management system in batches at the end of their shifts and not coincident to actual discharge events, leading to unintentional delays and uncertainty for incoming patients in areas such as Emergency and post-anesthesia care units as well as delays and bottlenecking pressure on staff involved in bed cleaning and patient transport. Alternately, nurses may delay the reporting of discharge information in order to defer additional admissions to the unit and thereby reduce workflow pressures, leading to cascading delays across the hospital.

Therefore, hospitals could benefit from a system to provide automated, unbiased control of discharge-related activities.

BRIEF SUMMARY

Certain examples provide systems and methods to monitor and control hospital operational systems based on occupancy data and medical orders.

An example healthcare workflow management and reasoning system includes a workflow engine including a first particularly programmed processor to monitor one or more medical orders from one or more hospital information systems to identify a condition indicating that a first patient in a first room is ready for discharge. The example healthcare workflow management and reasoning system includes a sensing component including a second processor to gather occupancy data regarding the first patient in the first room and transmit the occupancy data to the workflow engine. The example workflow engine controls one or more hospital operational systems to trigger cleaning of the first room, lighting settings for the first room, and transportation of a second patient to the first room based on occupancy data from the sensing component.

An example computer-implemented method includes monitoring, via a workflow engine including a first particularly programmed processor, one or more medical orders from one or more hospital information systems. The example computer-implemented method includes identifying, based on the monitored one or more medical orders, a condition indicating that a first patient in a first room is ready for discharge. The example computer-implemented method includes gathering, via a sensing component including a second processor, occupancy data regarding the first patient in the first room. The example computer-implemented method includes transmitting the occupancy data to the workflow engine. The example computer-implemented method includes controlling, via the workflow engine, one or more hospital operational systems to trigger cleaning of the first room, lighting settings for the first room, and transportation of a second patient to the first room based on occupancy data from the sensing component.

An example tangible computer-readable storage medium includes instructions which, when executed, particularly configure a processor to implement a method. The example method includes monitoring, via a workflow engine including a first particularly programmed processor, one or more medical orders from one or more hospital information systems. The example method includes identifying, based on the monitored one or more medical orders, a condition indicating that a first patient in a first room is ready for discharge. The example method includes gathering, via a sensing component including a second processor, occupancy data regarding the first patient in the first room. The example method includes transmitting the occupancy data to the workflow engine. The example method includes controlling, via the workflow engine, one or more hospital operational systems to trigger cleaning of the first room, lighting settings for the first room, and transportation of a second patient to the first room based on occupancy data from the sensing component.

Example computer-readable media, systems, and/or other apparatus can be used to implement methods disclosed herein.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

FIG. 11 shows an example table of lights, controls, and relays using presently described technology.

DETAILED DESCRIPTION

Figure 1:
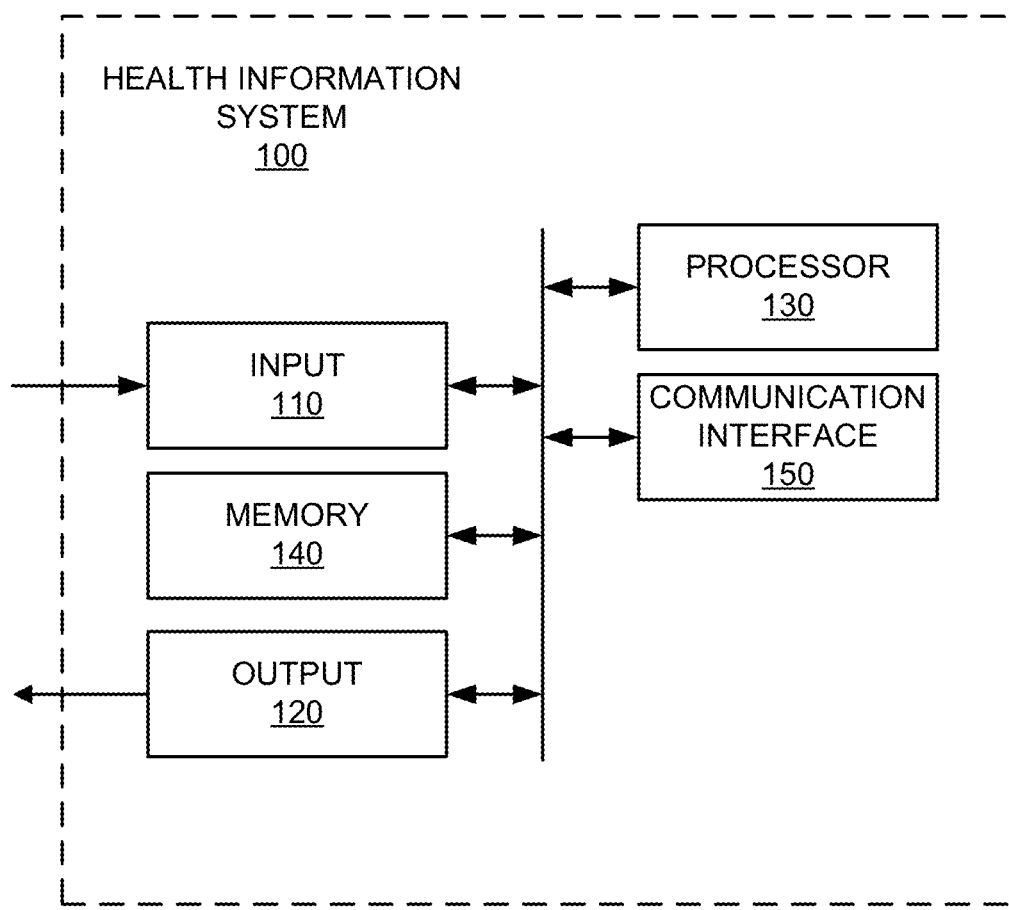
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Certain examples provide a portfolio of occupancy sensing modalities, such as for use in one or more hospital rooms, coupled to an automated reasoning engine which interprets physical events in context with medical orders to provide automated dynamic control of operational workflows within complex operations such as hospitals. This may include initiating and guiding events related to the discharge of a hospital patient, such as clinical activities, bed cleaning, bed reassignment and transfer of new admissions into appropriate beds. This combination of sensing and automated resource assignment and control helps proactively managing and optimizing a facility's capacity utilization, and minimizing the waiting times experienced by its patients.

Most hospital activities require coordination of people and assets to execute a task. Additionally, transition times are involved to move patient to patient for care providers and the assets they use. Having a high fidelity forecast of the future enables the beneficial sequencing of these task and resources. While having awareness of current state information is valuable, such as an empty bed, even more beneficial is having an ability to anticipate these states, monitor their status, update their forecasts, and dynamically control workflow in anticipation of a next state. Having an accurate state such as room occupancy reduces forecast error such as provided in the presently disclosed methods and systems.

Certain examples enable hospital capacity management to be more precise, especially as capacity management relates to speeding up room turnover, thus deriving more bed capacity especially at times of day at which a healthcare facility's population census can be equal to or over 100%.

Certain examples of resource sensing and control beneficially enable interaction of lighting and environmental controls (e.g., heating, ventilating and air conditioning (HVAC)) with clinical activity. Certain examples enable energy efficiency with lighting and HVAC closed loop control.

Certain examples provide an automated workflow and control engine ("workflow engine") which probabilistically optimizes resource utilization through time, coupled to one or more instances of an occupancy-sensing component ("sensing component"). The workflow engine activates and guides timely performance of operational processes related to hospital patient discharge, including but not limited to initiation of room cleaning, patient transport and updating of patient and bed status in electronic systems. Using the workflow engine can reduce admission waiting times experienced by patients and improve a hospital's overall throughput and capacity utilization. A hospital may have a limited number of inpatient beds available, and any unnecessary delays in identifying or reporting discharges and initiating discharge-related operational processes can cause cascading delays throughout the facility. A key advance in the art is the management of resources through time so as to probabilistically optimize one or more operational states of the hospital, a problem arising from computer-assisted scheduling and operational control of a hospital or other healthcare facility and a limitation in currently computing technology.

The workflow engine monitors data in the hospital's information systems in order to identify inpatients (e.g., patients currently assigned to hospital beds or rooms) who may be candidates for near-term discharge. Once a suitable candidate is found, the workflow engine activates one or more sensing components which are equipped to monitor that patient's assigned location. The sensing component (or components) determine and monitor the occupancy status of the room and report this to the workflow engine. The workflow engine also monitors hospital information systems to determine if any patients are waiting for admission into the room. When the original patient departs this room and does not return for a suitable interval (e.g., 15 minutes, 30 minutes, one hour, etc.), the workflow engine is empowered to automatically initiate and guide actions to ensure the timely admission of a different patient into the room. These actions include activating or scheduling bed cleaning staff to prepare the room, and then automatically activating or scheduling hospital transportation staff to transport the new patient to the room. The workflow engine can also update hospital information systems as to the discharge status of the patient (e.g., based on whether or not they have departed the room), and the status of cleaning and transportation staff activity.

The sensing component may integrate two or more types of sensors to ensure high detection accuracy, including the detection of a very still patient (e.g., sleeping under a blanket) in dark conditions. The sensors may be located outside of the patient's clinical area in the room, such as above ceiling tiles, to avoid privacy concerns. The sensing and occupancy component may also facilitate control of the room's environmental systems including lighting and temperature, based on information from the workflow engine as well as occupancy signals from the room itself.

Certain examples also provide anticipatory monitoring and controlling, at a current time and in the near future, of activities that will cause schedule events to occur in a timely way so as to reduce delays and under-utilized resources through time. Having a forecast and dynamic state information to update the status of the forecast's assumptions enables more accurate control of resource(s) through time and dynamic changes to an original schedule. For example, an example monitored room helps to prevent an incorrectly identified or labeled "not occupied" or "occupied" current state from propagating into future forecast error.

As will be described further below, certain examples can integrate with and operate in a variety of healthcare environments and impact a variety of healthcare scenarios and data through sensing, decision support, workflow management, and control. The following section provides some context and example environment for the presently disclosed technology described further in the subsequent section below.

II. Example Operating Environments

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. Example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of example system 100 can be integrated in one device or distributed over two or more devices.

Example input 110 may include a keyboard, a touchscreen, a mouse, a trackball, a track pad, optical barcode recognition, voice command, etc. or combination thereof used to communicate an instruction or data to system 100. Example input 110 may include an interface between systems, between user(s) and system 100, etc.

Example output 120 can provide a display generated by processor 130 for visual illustration on a monitor or the like. The display can be in the form of a network interface or graphic user interface (GUI) to exchange data, instructions, or illustrations on a computing device via communication interface 150, for example. Example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

Example processor 130 includes hardware and/or software configuring the hardware to execute one or more tasks and/or implement a particular system configuration. Example processor 130 processes data received at input 110 and generates a result that can be provided to one or more of output 120, memory 140, and communication interface 150. For example, example processor 130 can take user annotation provided via input 110 with respect to an image displayed via output 120 and can generate a report associated with the image based on the annotation. As another example, processor 130 can process updated patient information obtained via input 110 to provide an updated patient record to an EMR via communication interface 150.

Example memory 140 may include a relational database, an object-oriented database, a data dictionary, a clinical data repository, a data warehouse, a data mart, a vendor neutral archive, an enterprise archive, etc. Example memory 140 stores images, patient data, best practices, clinical knowledge, analytics, reports, etc. Example memory 140 can store data and/or instructions for access by the processor 130. In certain examples, memory 140 can be accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 is not searchable. For example, a patient's data can be encrypted with a unique patient-owned key at the source of the data. The data is then uploaded to memory 140. Memory 140 does not process or store unencrypted data thus minimizing privacy concerns. The patient's data can be downloaded and decrypted locally with the encryption key.

For example, memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

Example communication interface 150 facilitates transmission of electronic data within and/or among one or more systems. Communication via communication interface 150 can be implemented using one or more protocols. In some examples, communication via communication interface 150 occurs according to one or more standards (e.g., Digital Imaging and Communications in Medicine (DICOM), Health Level Seven (HL7), ANSI X12N, etc.). Example communication interface 150 can be a wired interface (e.g., a data bus, a Universal Serial Bus (USB) connection, etc.) and/or a wireless interface (e.g., radio frequency, infrared (IR), near field communication (NFC), etc.). For example, communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
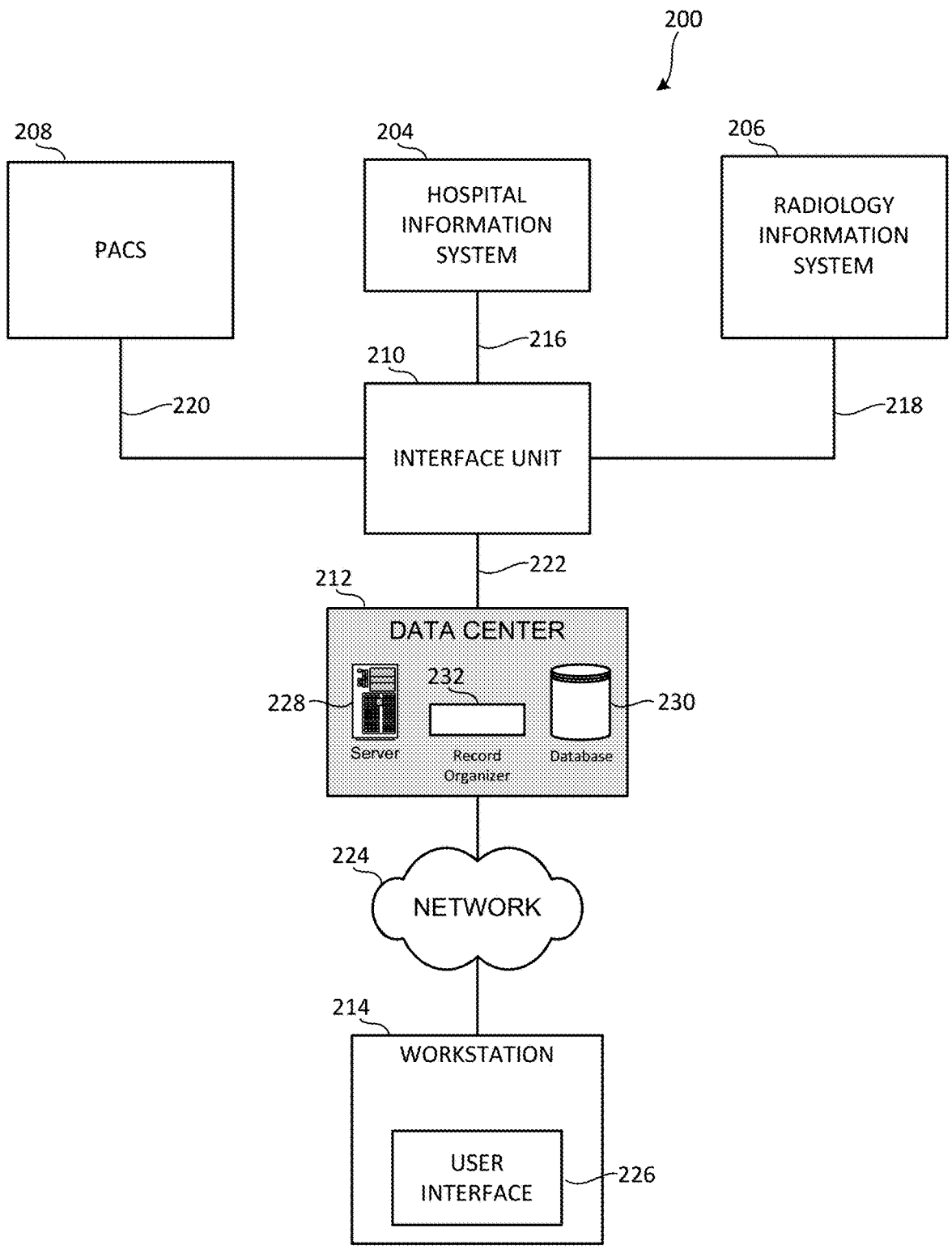
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. Example healthcare system 200 includes a HIS 204, a RIS 206, a PACS 208, an interface unit 210, a data center 212, and a workstation 214. In the illustrated example, HIS 204, RIS 206, and PACS 208 are housed in a healthcare facility and locally archived. However, in other implementations, HIS 204, RIS 206, and/or PACS 208 may be housed within one or more other suitable locations. In certain implementations, one or more of PACS 208, RIS 206, HIS 204, etc., may be implemented remotely via a thin client and/or downloadable software solution. Furthermore, one or more components of the healthcare system 200 can be combined and/or implemented together. For example, RIS 206 and/or PACS 208 can be integrated with HIS 204; PACS 208 can be integrated with RIS 206; and/or the three example information systems 204, 206, and/or 208 can be integrated together. In other example implementations, healthcare system 200 includes a subset of the illustrated information systems 204, 206, and/or 208. For example, healthcare system 200 may include only one or two of HIS 204, RIS 206, and/or PACS 208. Information (e.g., scheduling, test results, exam image data, observations, diagnosis, etc.) can be entered into HIS 204, RIS 206, and/or PACS 208 by healthcare practitioners (e.g., radiologists, physicians, and/or technicians) and/or administrators before and/or after patient examination. One or more of the HIS 204, RIS 206, and/or PACS 208 can communicate with equipment and system(s) in an operating room, patient room, etc., to track activity, correlate information, generate reports and/or next actions, and the like.

The HIS 204 stores medical information such as clinical reports, patient information, and/or administrative information received from, for example, personnel at a hospital, clinic, and/or a physician's office (e.g., an EMR, EHR, PHR, etc.). RIS 206 stores information such as, for example, radiology reports, radiology exam image data, messages, warnings, alerts, patient scheduling information, patient demographic data, patient tracking information, and/or physician and patient status monitors. Additionally, RIS 206 enables exam order entry (e.g., ordering an x-ray of a patient) and image and film tracking (e.g., tracking identities of one or more people that have checked out a film). In some examples, information in RIS 206 is formatted according to the HL-7 (Health Level Seven) clinical communication protocol. In certain examples, a medical exam distributor is located in RIS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a Wide Area Network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless Local Area Network, and/or a wired or wireless Wide Area Network. In some examples, interface unit 210 also includes a broker (e.g., a Mitra Imaging's PACS Broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), interface unit 210 translates or reformats (e.g., into Structured Query Language ("SQL") or standard text) the medical information, such as medical reports, to be properly stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and easily retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc. Workstation 214 is capable of implementing a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226. In some examples, the administrator adjusts one or more settings or outcomes via user interface 226.

Example data center 212 of FIG. 2 is an archive to store information such as images, data, medical reports, and/or, more generally, patient medical records. In addition, data center 212 can also serve as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In some examples, data center 212 can be spatially distant from HIS 204, RIS 206, and/or PACS 208.

Example data center 212 of FIG. 2 includes a server 228, a database 230, and a record organizer 232. Server 228 receives, processes, and conveys information to and from the components of healthcare system 200. Database 230 stores the medical information described herein and provides access thereto. Example record organizer 232 of FIG. 2 manages patient medical histories, for example. Record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network, for example. In certain examples, all or part of system 200 can also be provided via platform as a service (PaaS), infrastructure as a service (IaaS), etc. For example, system 200 can be implemented as a cloud-delivered Mobile Computing Integration Platform as a Service. A set of consumer-facing Web-based, mobile, and/or other applications enable users to interact with the PaaS, for example.

C. Industrial Internet Examples

The Internet of things (also referred to as the "Industrial Internet") relates to an interconnection between a device that can use an Internet connection to talk with other devices on the network. Using the connection, devices can communicate to trigger events/actions (e.g., changing temperature, turning on/off, providing a status, etc.). In certain examples, machines can be merged with "big data" to improve efficiency and operations, provide improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
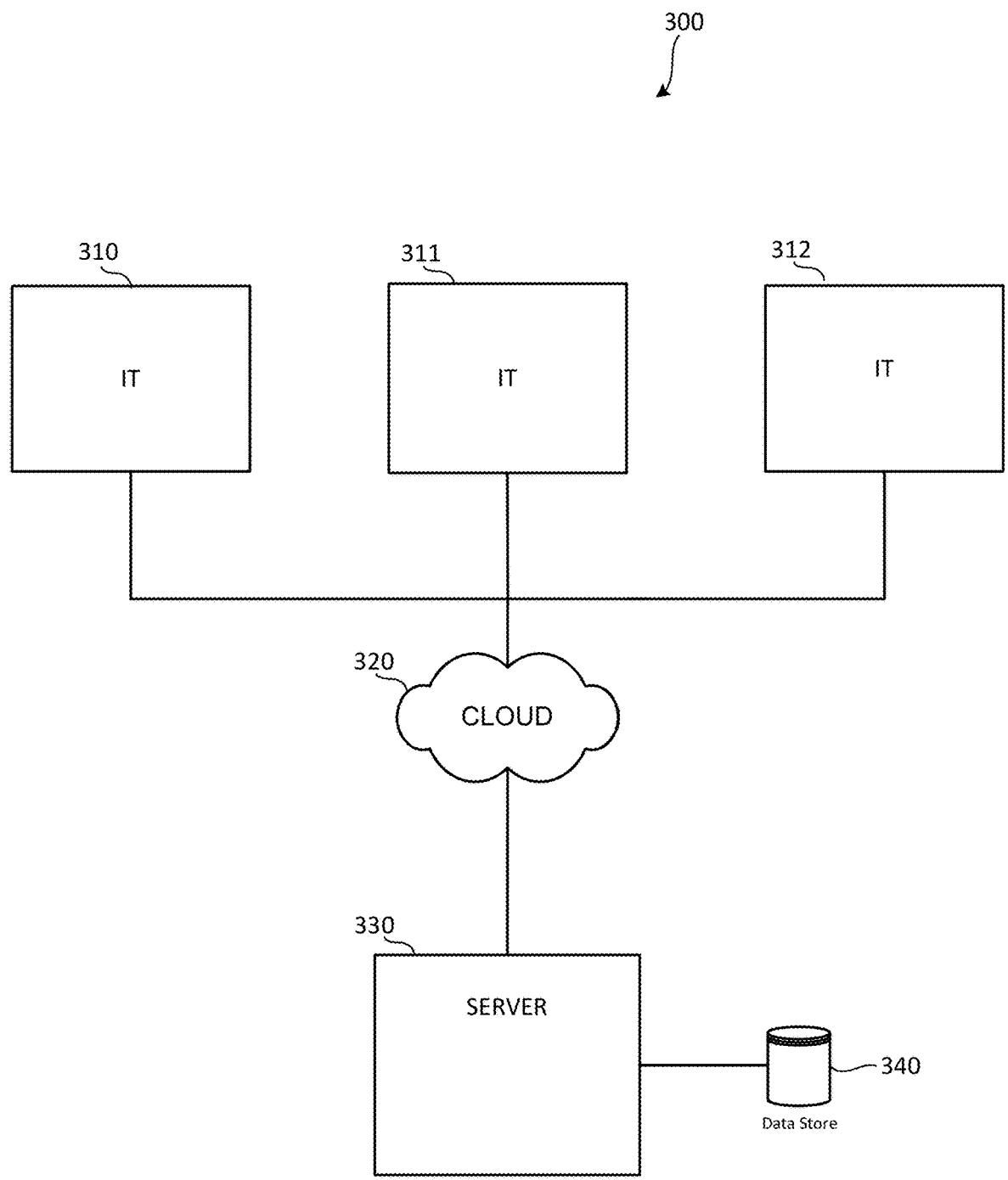
FIG. 3 shows an example industrial internet configuration including a plurality of health-focused systems.

FIG. 3 illustrates an example industrial internet configuration 300. Example configuration 300 includes a plurality of health-focused systems 310-312, such as a plurality of health information systems 100 (e.g., PACS, RIS, EMR, etc.) communicating via industrial internet infrastructure 300. Example industrial internet 300 includes a plurality of health-related information systems 310-312 communicating via a cloud 320 with a server 330 and associated data store 340.

As shown in the example of FIG. 3, a plurality of devices (e.g., information systems, imaging modalities, etc.) 310-312 can access a cloud 320, which connects the devices 310-312 with a server 330 and associated data store 340. Information systems, for example, include communication interfaces to exchange information with server 330 and data store 340 via the cloud 320. Other devices, such as medical imaging scanners, patient monitors, etc., can be outfitted with sensors and communication interfaces to enable them to communicate with each other and with the server 330 via the cloud 320.

Thus, machines 310-312 within system 300 become "intelligent" as a network with advanced sensors, controls, analytical based decision support and hosting software applications. Using such an infrastructure, advanced analytics can be provided to associated data. The analytics combines physics-based analytics, predictive algorithms, automation, and deep domain expertise. Via cloud 320, devices 310-312 and associated people can be connected to support more intelligent design, operations, maintenance, and higher server quality and safety, for example.

Using the industrial internet infrastructure, for example, a proprietary machine data stream can be extracted from a device 310. Machine-based algorithms and data analysis are applied to the extracted data. Data visualization can be remote, centralized, etc. Data is then shared with authorized users, and any gathered and/or gleaned intelligence is fed back into the machines 310-312.

D. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

E. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, executing orders for specific care, signing off on orders for a discharge, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, dispatching room cleaning and/or patient transport, and/or any other action useful in processing healthcare information or causing critical path care activities to progress. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. Example Sensing and Situational Awareness Systems and Methods

Certain examples provide a workflow and reasoning engine ("workflow engine") coupled to one or more occupancy sensors (also referred to herein as "sensing component(s)"). In an environment such as a hospital, the workflow engine can be connected to one or more existing hospital information systems, and the sensing components can be installed in patient rooms. The workflow engine can assess the current state of various elements related to patient flow and then initiate and guide operational activities which may include the activation of staff to clean patient rooms and transfer patients into appropriate rooms and update the discharge or transfer status of patients, for example.

Figure 4:
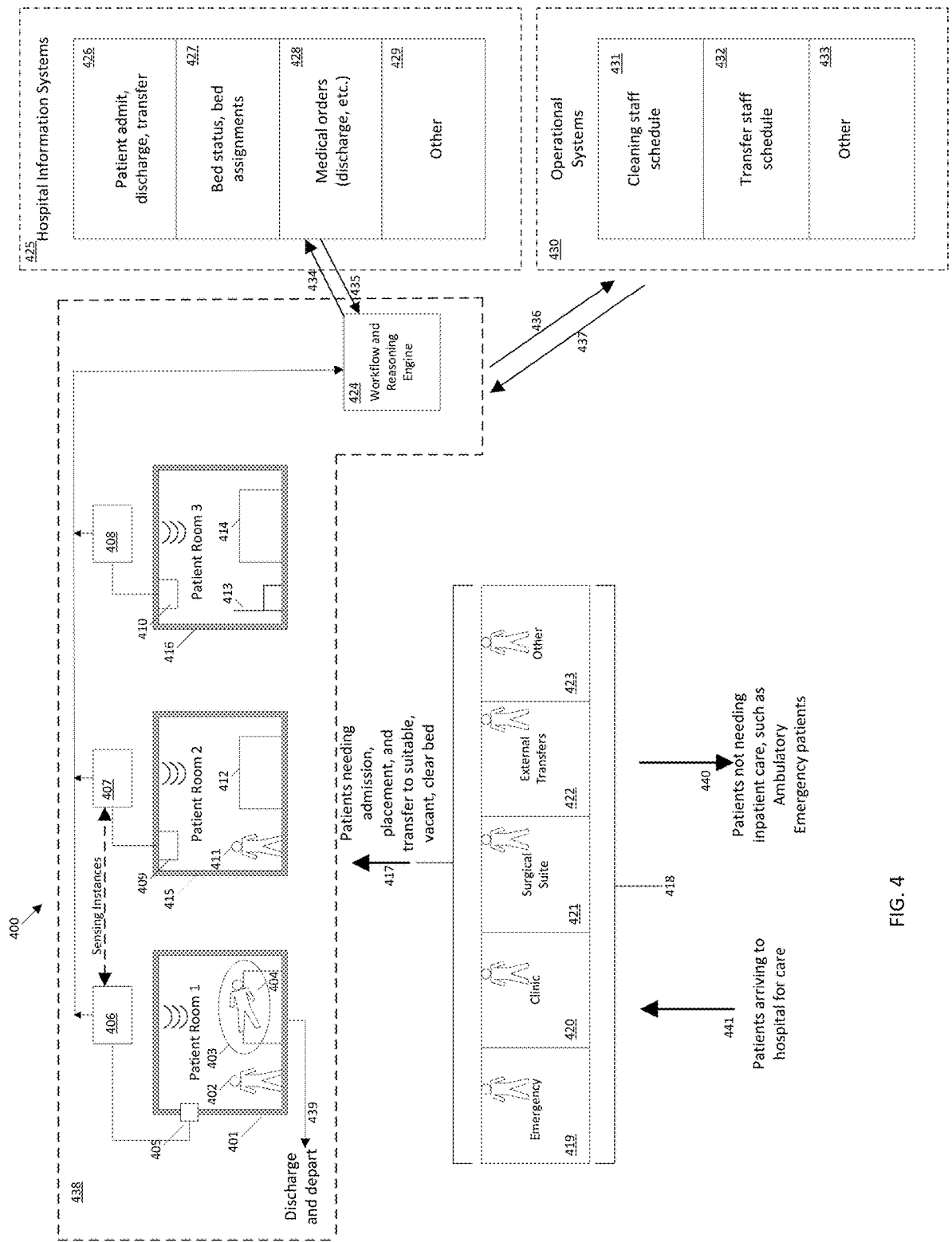
FIG. 4 illustrates a schematic of an example sensing and reasoning network in the context of a hospital environment.

FIG. 4 illustrates a schematic of an example sensing and reasoning network 438 in the context of a hospital environment 400. As shown in the example of FIG. 4, a workflow engine 424 and a plurality of sensing components 406-408 (e.g., Doppler sensor, optical sensor, etc.) are installed in patient rooms 401, 415, 416. Each room 401, 415, 416 includes one or more people 402, 403, 411 (e.g., patients, physicians, other personnel, etc.), furniture 404, 412, 413, 414 (e.g., patient bed, chair, examination table, etc.), and electronics 405, 409, 410 (e.g., lighting, fan, camera, detector, etc.). The sensing components 406-408 gather data based on objects, movement, and/or other state/status information in the rooms 401, 415, 416, for example.

The workflow engine 424 is also linked to a hospital information system 425 which may include multiple data systems 426-429 (e.g., a patient admit discharge transfer (ADT) system, a bed status/assignment system, a medical order system, etc.). The workflow engine 424 is also connected to existing hospital operations management systems 430 (also referred to as hospital operational systems or operational systems, for example) which may include various scheduling and staff (resource) control systems 431-433, for example.

The workflow engine 424 can manage the timely transition of patients throughout the hospital system 400. Patients requiring care 441 may arrive at the hospital via a number of circumstances 419-423 including through the Emergency room 419, from surgery in an operating room 421 or other methods (e.g., clinic 420, external transfer 422, other 423). Although some arrivals may be able to later depart 440 without an inpatient stay, many patients 417 will require further care in an inpatient bed 404.

In many hospitals, inpatient bed capacity is highly utilized, resulting in a scarcity of suitable inpatient beds 404, 412, 414 available for new admissions which then slows and restricts the process of admission 417. Inpatient bed capacity is released when a current patient 403, 411 occupying the bed 404, 412 is discharged 439 from the hospital. However, before a new admission can occupy this bed 404, 412, the previous discharge must be made known to hospital staff and recorded in hospital information systems 426, 427. Then the bed and room must be cleaned and the new patient transported to the room. This discharge and cleanup process is frequently delayed due to a lack of awareness of the specific timing of the departure of a discharging patient as well as delays or gaps in time arising due to manual activation of operational activities, for example.

Using the sensing components 406, 407, 408 and the workflow engine 424, certain examples improve and streamline a discharge and transfer process through automated detection of departure, and automated activation and guidance of appropriate operational activities. Automated detection of departure with automated activation and guidance of appropriate operational activity can help to reduce waiting times for admission experienced by patients in hospital or other healthcare facility environments such as Emergency and post-anesthesia care units while also improving the hospital's bed throughput, for example.

An example of the system's operation includes evaluating hospital data to identify a specific patient in a room who is scheduled for discharge. For the identified patient, the example system 400 confirms that the patient is not scheduled for another medical procedure which would eventually return them to the same room. The example system 400 monitors the patient's room to detect if and when the patient departs the hospital. Then, the example system 400 initiates and guides operational activities such as activating bed cleaning staff to turn over the room and activating transportation staff to transfer another suitable patient (waiting for admission) into the now-vacant room, for example.

Various instances of the occupancy sensing component 406-408 can be installed in patient rooms 401. These components 406-408 may be positioned above ceiling tiles or in other fashions which do not compromise patient privacy, and may be able to harvest power from existing lighting 409 or other components 405, 410. The sensing components 406-408 can be activated by the workflow engine 424 to monitor specific rooms to determine whether they are currently in active use. Based on a combination of sensing results and hospital information system data, the workflow engine 424 can determine whether to activate specific hospital operational functions.

Figure 5:
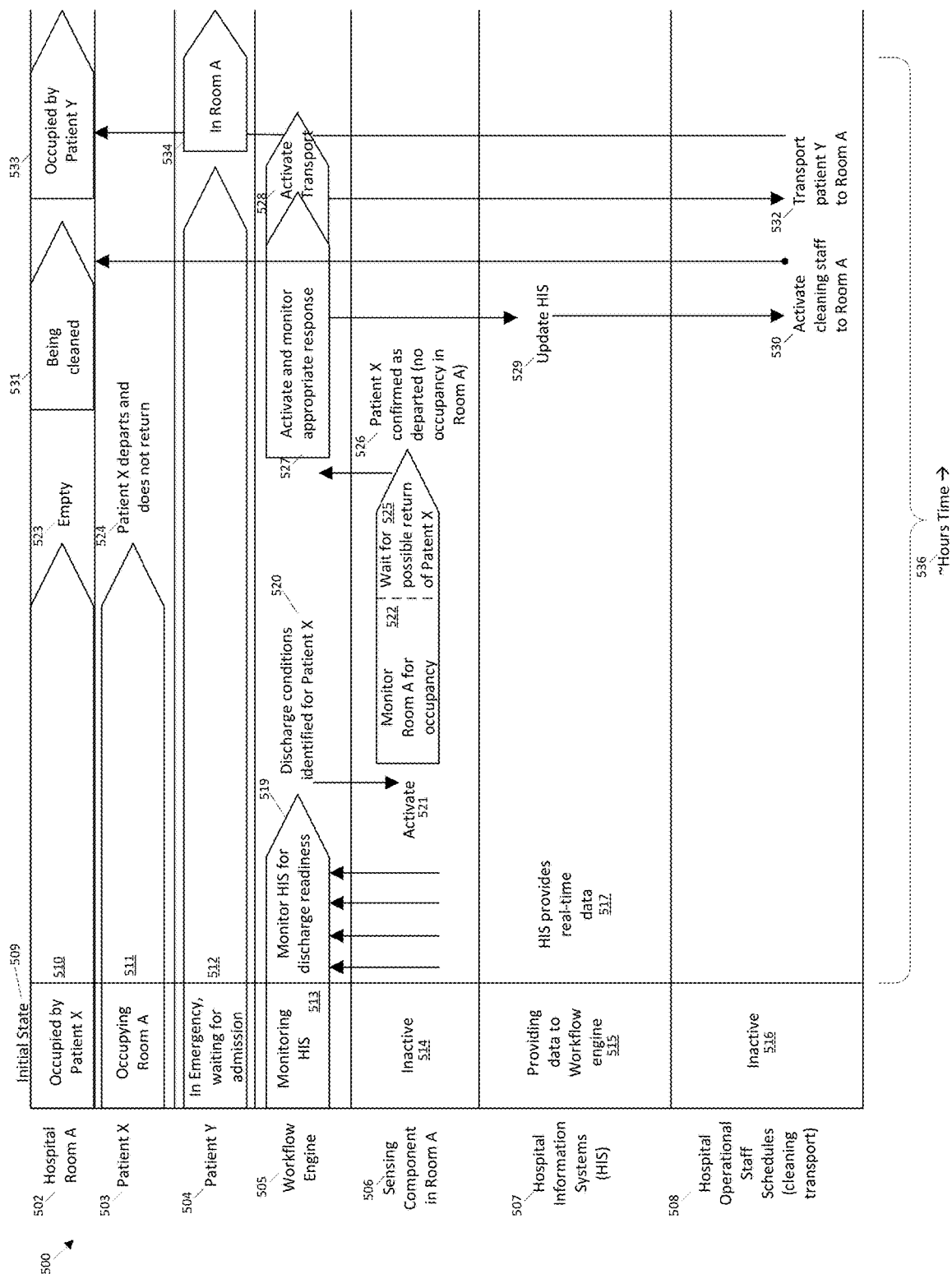
FIG. 5 illustrates a sample timeline of events relating to operation of presently disclosed technology with respect to a single hospital room, across a time span of several hours.

FIG. 5 illustrates a sample timeline 500 of events relating to the operation of the presently disclosed technology with respect to a single hospital room 502, across a timespan 536 of several hours. The example of FIG. 5 assumes that only one patient is admitted per room, and, therefore, uses the terms "bed" and "room" interchangeably. In an assumed initial state 509 or starting condition, Room A 502 is occupied by a Patient X 503 while a Patient Y 504 is in the hospital's Emergency department waiting for admission to a bed such as bed 502.

A workflow engine 505 continuously monitors 519 various hospital information systems 507 to identify patients who are consistent with specified conditions for timely discharge. At a point in time (e.g., in a workday or shift) 520, the workflow engine 505 determines that Patient X 503 meets the discharge conditions, and the workflow engine 505 activates 521 a sensing component 506 installed in Room A 502. The sensing component 506 then monitors 522 Room A 502 to capture one or more indications regarding whether the room 502 is currently occupied.

After the start of monitoring 522 but prior to Patient X's final departure 524 from the room 502, Patient X 503 may depart Room A 502 briefly and return within a short interval, such as a few minutes. These temporary departures are ignored by the sensing component 506 and are not considered true final departures from the room. However, at some later point in the day 524, Patient X 503 departs Room A 502 and does not return. The sensing component 506 waits 525 a suitable interval (e.g., 30 minutes, 45 minutes, etc.) to determine whether the patient will again return to the room, but, once the given interval has passed 526, the sensing component 506 notifies the workflow engine 505 that Room A 502 is no longer occupied.

Once Room A 502 is determined to be unoccupied 526, the workflow engine 505 initiates 527 a series of operational activities to help ensure the timely placement of a new patient into the room. The workflow engine 505 notifies 529 the hospital information system(s) 507 of Patient X's status as departed or discharged, and then activates 530 cleaning staff to prepare Room A 502. Once the room cleaning 531 is complete, this information is relayed back 528 to the workflow engine 505, which then activates 532 transportation staff to transport Patient Y 504 to Room A 502. The process is completed when Patient 504 occupies Room A 533, 534.

As shown in the example of FIG. 5, the Hospital Room A's 502 timeline advances from an initial state 509 in which the room 502 is occupied by Patient X 503 through a waiting or determination monitoring period 510 in which room occupancy sensor 506 data and hospital information system 507 data 517 is analyzed to determine that the room 502 is now empty 523. After the room 502 is classified as empty 523, the room is then cleaned 531 by hospital operational staff 508, who had been inactive 516 awaiting instruction. After the room 502 has been cleaned 531, then Patient Y 504 occupies 533 the room 502.

From the viewpoint of Patient X 503, he or she is initially occupying room A 502. After a period of time 511 in Room A 502, Patient X 503 departs Room A 502 and does not return 524. For Patient Y 504, he or she is initially in the emergency department awaiting admission. After a period of time 512, Patient Y 504 is admitted 534 into Room A 502.

In the example of FIG. 5, the workflow engine 505 begins by monitoring 513 the hospital information system(s) 507. The HIS 507 provides real-time data 517 to the workflow engine 505 regarding Patient X 503. Based on the real-time HIS data 517, the workflow engine 505 identifies 520 discharge conditions for Patient X 503. Once discharge conditions have been identified 520, the workflow engine 505 activates 521 the sensing component(s) 506 in Room A 502 to obtain sensor data regarding occupancy, movement, object(s), etc., in Room A 502. Based on the sensor data, the workflow engine 505 initiates a series of operational activities and monitors responses 527 to prepare Room A 502 for a new patient (Patient Y 504). The workflow engine 505 notifies 529 the hospital information system(s) 507 of Patient X's 503 status as departed or discharged, and then activates 530 cleaning staff to prepare Room A 502 for the next patient. The workflow engine 505 receives an indication that room cleaning 531 is complete and then alerts transportation staff 532 to activate transport 528 of Patient Y 504 to Room A 502.

For the sensing component(s) 506 in Room A, the example of FIG. 5 shows that the sensor(s) 506 begins in an inactive state 514. When the sensor(s) 506 receive an activation signal or command 521 from the workflow engine 505, the sensor(s) 506 monitor 522 Room A 502 for occupancy. For example, one or more sensing components 506 monitor Room A 502 to obtain sensor data (e.g., Doppler sensor data, optical sensor data, infrared sensor data, other motion sensor data, radio frequency identification data, etc.) regarding occupancy, movement, object(s), etc., in Room A 502. Based on the monitoring, the sensor(s) 506 wait for possible return of Patient X 503 to Room A 502. After a time period (e.g., an elapsed period of time determined based on average procedure, protocol and/or delay time associated with activity of Patient X 503 and/or a general reference patient, for example), Patient X 503 is confirmed as departed 526 from Room A 502. That is, sensor(s) 506 confirms that Room A 502 is now unoccupied.

As shown in the example of FIG. 5, the hospital information system(s) HIS 507 provides 515 data to the workflow engine 505. Real-time data is provided 517 with respect to patient, room, procedure, etc., by the HIS 507 to the workflow engine 505 to determine a discharge readiness 519 for Patient A 503. The workflow engine 505 updates the HIS 507 with status information 529 regarding departure or discharge of Patient X 503, for example.

Additionally, as illustrated in the example of FIG. 5, hospital operations staff scheduling 508 is initially inactive 516 and is then activated 530 by the HIS 507 and/or workflow engine 505 to schedule cleaning staff for Room A 502 and transport 532 Patient Y 504 to Room A 502.

Although this example focuses on a single room (Hospital Room A 502), the workflow engine 505 is capable of working with multiple patient rooms simultaneously. In such a case, the workflow engine 505 evaluates hospital information system data related to any patient in a room equipped with a sensing component 506, and can activate and communicate with multiple sensing components simultaneously.

Figure 6:
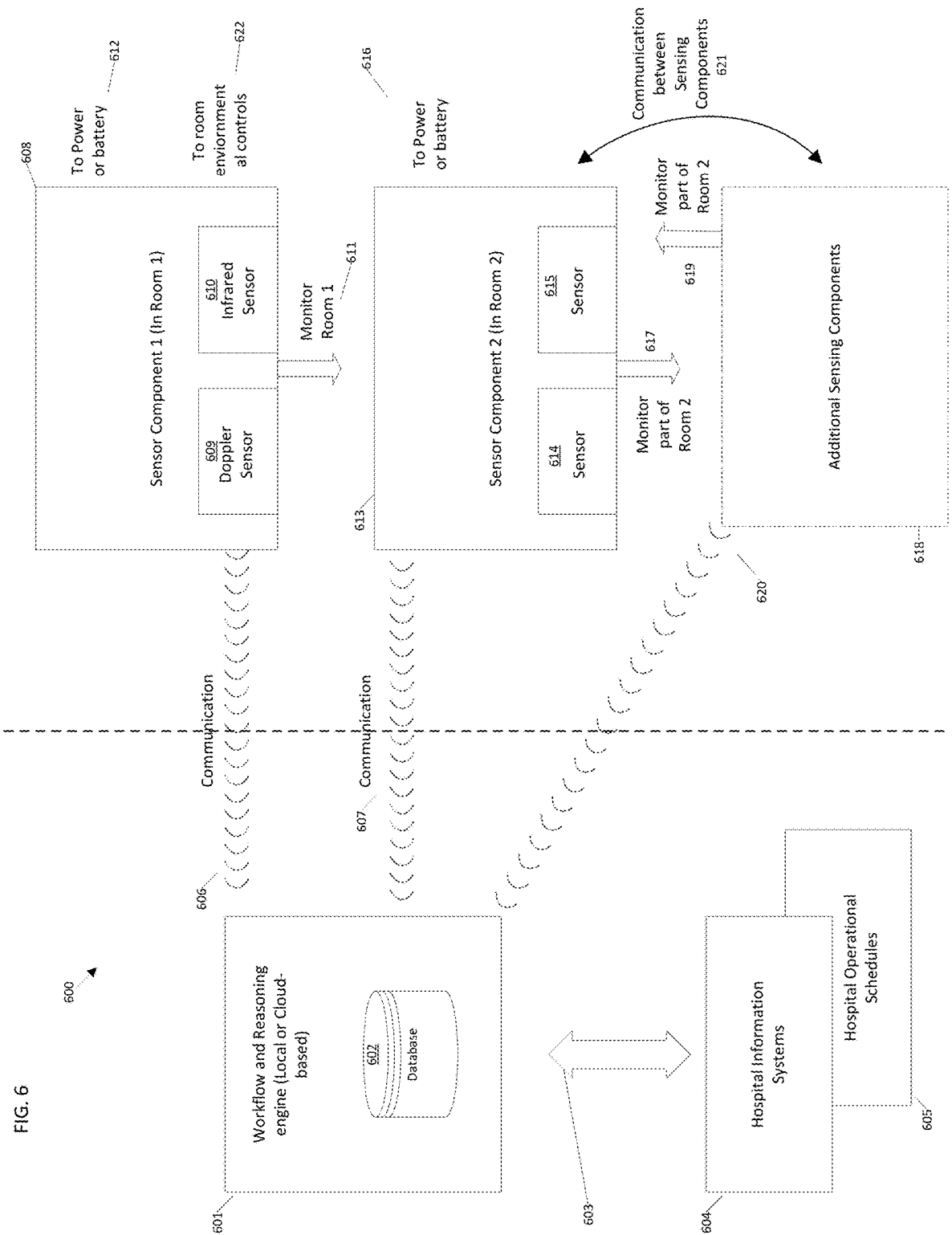
FIG. 6 illustrates various physical components of an example workflow sensing and reasoning system.

FIG. 6 illustrates various physical components of an example workflow sensing and reasoning system 600. The example system 600 includes a workflow engine 601 which may be physically located on hospital premises and/or hosted and managed elsewhere ("cloud-based"), for example. The workflow engine 601 includes a database 602, which maintains bi-directional information connections 603 to one or more hospital data systems 604 and/or hospital operational schedules 605 and also communicates 606, 607, 620 with one or more sensing components 608, 613, 618.

In the example of FIG. 6, sensing components 608, 613, 618 are located in patient rooms. A particular sensing component 608 may monitor an entire patient room 611 and all patients or beds contained within that room; or, alternatively, multiple sensing instances 613, 618 may be installed together to monitor various parts of a particular room (e.g., Room 2) concurrently 617, 619. All sensing components communicate 606, 607, 620 with the workflow engine 601. Individual sensing components 608, 613, 618 may also communicate with each other 621 in order to coordinate the concurrent monitoring of a specific location.

As shown in the example of FIG. 6, each sensing component 608, 613, 618 includes one or more sensors 609, 610, 614, 615 (e.g., Doppler sensor 609, infrared sensor 610, etc.) which are capable of detecting the occupancy and/or other monitoring of a specific room (e.g., Room 1, Room 2, etc.) by one or more individuals. The sensing components may also be connected to a power source 612, 616 and may be connected to the room's environmental controls 622 such as lighting, thermostat, etc. Further disclosure of an example sensing component is described below in connection with FIGS. 12-13.

Figure 7:
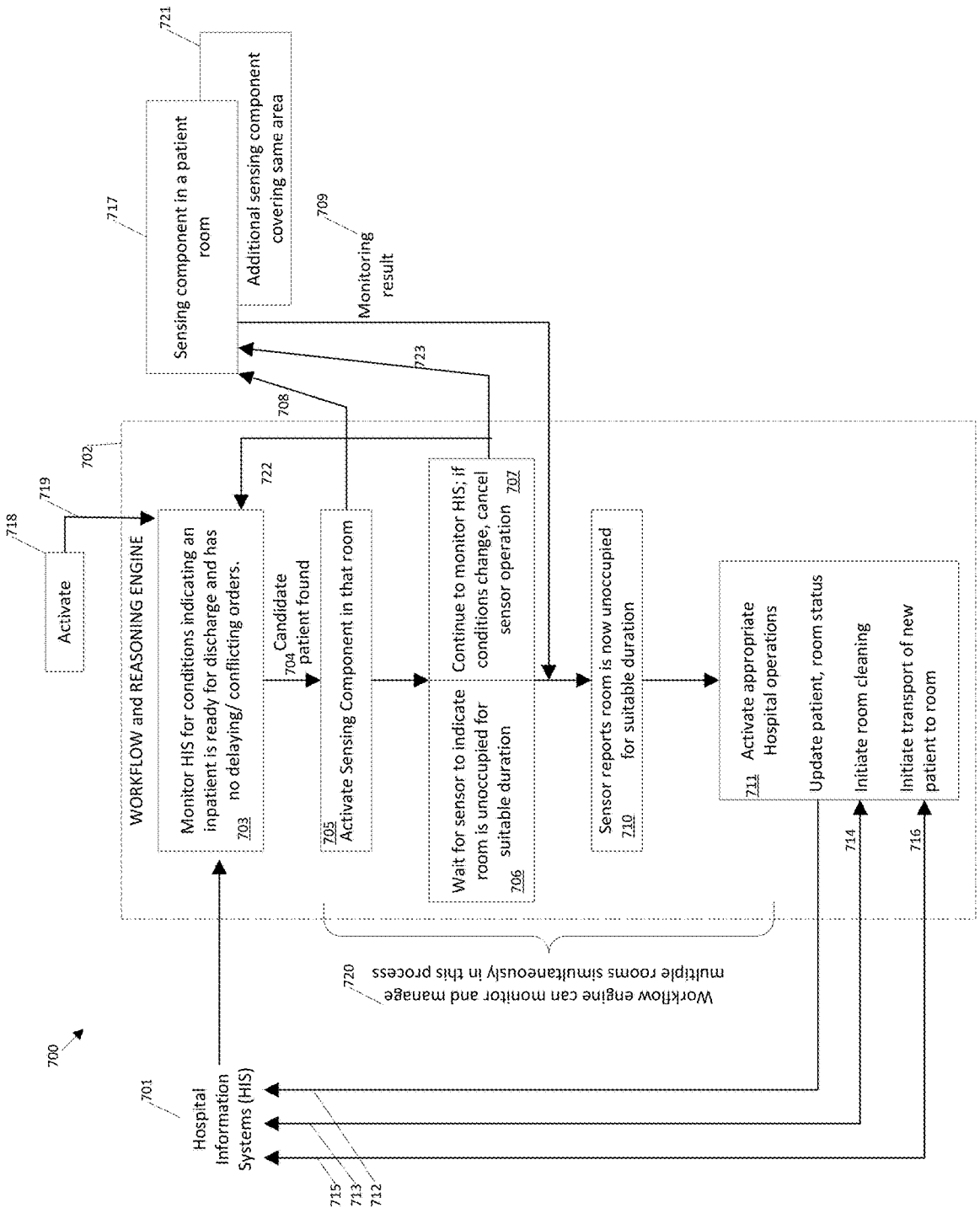
FIG. 7 is a block diagram illustrating an example operation and data flow of an example workflow and reasoning engine.

FIG. 7 is a block diagram illustrating an example operation and data flow 700 of an example workflow and reasoning engine 702, which has data connections 712-716 to various hospital information systems 701 and to one or more sensing components 717, 721. The workflow engine 702 may be activated by a signal 719 from an external agency 718, for example.

Once activated, a default or initial operational state 703 associated with the workflow engine 702 involves monitoring and evaluating data from the hospital information system(s) 701 to determine whether any current inpatient fits one or more conditions which have been pre-programmed to represent a typical patient who is ready for discharge. Conditions may include a presence of an active confirmed medical order for discharge written for the patient, confirmation that the patient is currently assigned to an inpatient bed, and an absence of other outstanding medical orders which would delay the patient's timely discharge or cause them to be removed from the room for some period of time (e.g., with the expectation that the patient would later return to the same room), etc. The workflow engine 702 only evaluates information for patients who are located in hospital rooms that have been equipped with one or more occupancy sensors 717, 721.

The workflow engine 702 can evaluate data for multiple patients concurrently 720, as well as managing multiple instances of discharge monitoring and operational activation for various patients, for example.

If and when the workflow engine 702 identifies 704 a patient meeting the specified discharge criteria (e.g., a "candidate" patient), the workflow engine 702 activates 705 one or more relevant sensing components 717, 721 through a communication signal 708. The workflow engine 702 determines the appropriate sensing component(s) 717, 721 to activate based on the patient's assigned location in hospital information system(s) 701. Depending on the configuration of the relevant sensing component(s) 717, 721, the area monitored for occupancy may include the patient's bed, areas around the bed including chairs, or the entire patient room.

Once the appropriate sensing components 717, 721 are activated 708, they begin to monitor the state of occupancy in the area corresponding to the patient's assigned location and report monitoring result information 709 to the workflow engine 702. The workflow engine 702 waits 706 for an indication from the sensing components 717, 721 that the room is no longer occupied. At the same time, the workflow engine 707 continues to monitor 707 hospital information system(s) 701 for an indication that the specified patient's discharge may be delayed or cancelled. Some examples of such indication include a retraction of the original discharge order, entry additional medical orders, etc. If an indication of change is detected, the workflow engine 702 terminates 723 activity of the relevant sensing component(s) 717, 721 and returns 722 to the state 703 of monitoring patient data for indication of a suitable discharge candidate.

If there is no indication that the discharge will be delayed or cancelled, then, after a period of time has elapsed (e.g., a pre-set or otherwise pre-determined period of time based on historical and/or otherwise measured protocol task and/or other procedure time, etc.), the sensing component(s) 717, 721 indicate 710 that the room is no longer occupied and has remained in this condition for a specified interval, such as thirty minutes. The workflow engine 702 then proceeds to activate and guide 711 activities intended to streamline the discharge and transfer process. The workflow engine 702 informs 712 hospital information systems that the room's original patient has departed so that discharge information can be updated. A message is sent 713 to bed cleaning staff and/or a staff scheduling system to initiate cleaning of the specified patient room. If there is a patient waiting for admission to this particular room or bed, once information is received 714 that the room has been cleaned, the workflow engine 702 automatically notifies 715 the hospital's transportation staff and/or scheduling system to transport the new patient into the cleaned room. The hospital's patient transportation data system 701 indicates 716 that the new patient has been transported to the room.

Figure 8:
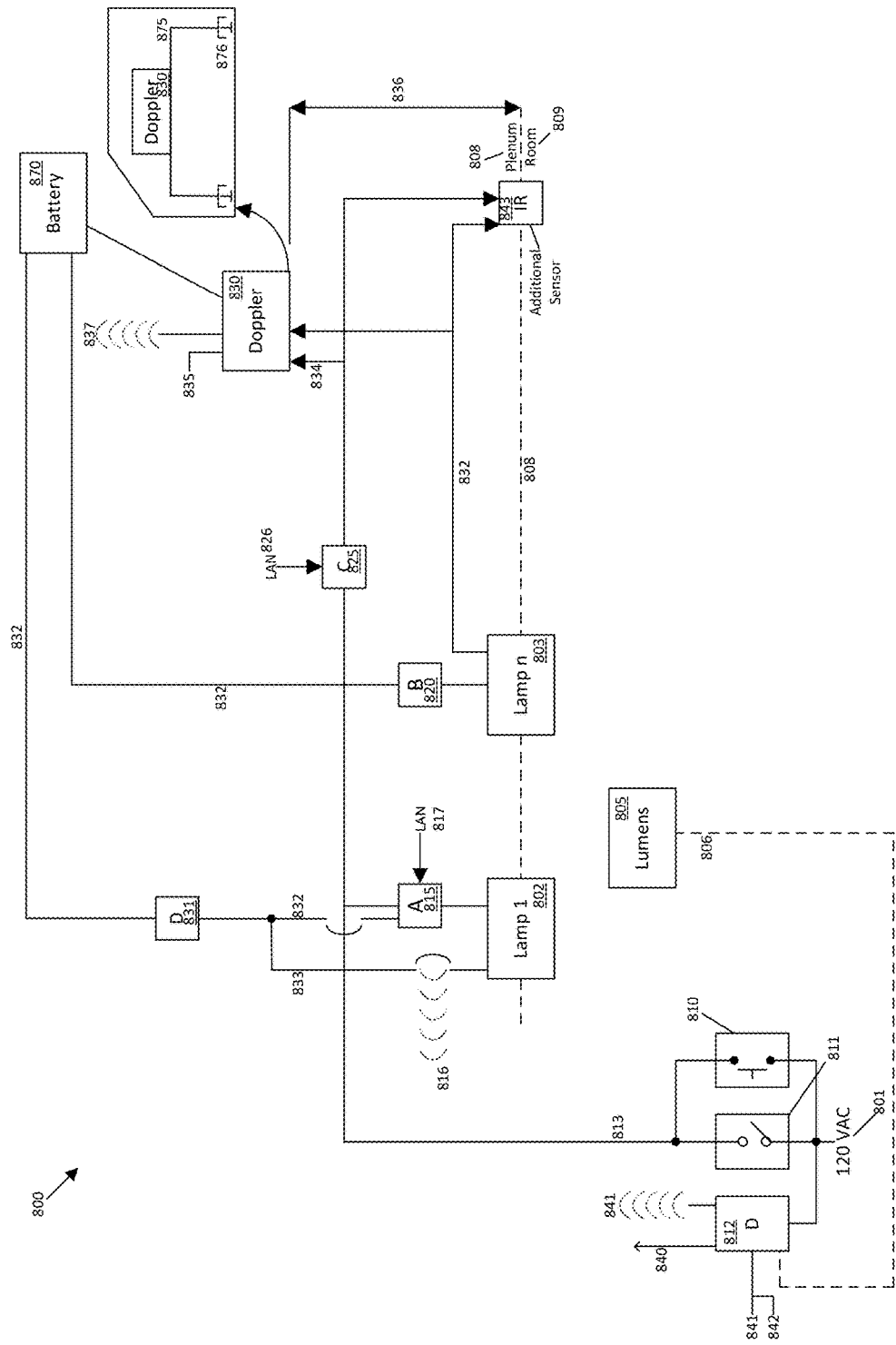
FIG. 8 shows example power management features.

FIG. 8 shows example power management features for sensing, lighting, controlled space activity interaction with protocols, lumen and HVAC control and physical placement components, to be located in or around a patient room.

The sensing, lamps and communications systems 800 consume power 801, such as 120 VAC 60 Hz in North America or 220 VAC 50 Hz in Europe. Power is consumed by one or more components intermittently, such as when a light is switched on 811, etc. Power is consumed continuously for components of the system 800 that are in active use at all times 812, such as a wireless communications network, a radiofrequency identification (RFID) sensor 841, a remotely switched device 840 controlled 812 from computer activation, etc. Power is also consumed as needed, such as for automated lighting or to automatically power an energy storage device 870 (e.g., a battery, etc.) as a function of its charge state, etc. In some examples, a pattern of switched power use can be implemented by the system 800 such that the system 800 is adequately powered by line voltage 801 or stored power 870.

Line voltage 801 is provided to one or more of the system's devices such as lamps 802, 803, a Doppler sensor 830, an energy store 870 and/or an additional sensing system 843 (e.g., IR sensor, optical sensor, etc.). Power may be directly connected or controlled by relays 815, 820, 825, 831. Relays 815, 820, 825, 831 are powered, optionally, by line voltage 801 or electrical power provided via Local Area Network (LAN) 817, 826. Relays 815, 820, 825, 831, when used, direct energy sources to devices 802, 803, 830 which beneficially use power when controlled to do so by the disclosed control system.

In one example embodiment, Lamp 1 802 is switched on by relay 'A' 815 which directs voltage 813, 810 and/or 811 to the lamp 802. In another example, Lamp 1 802 is powered with an energy storage device 870. A voltage 832 of the energy storage device 870 is directed by relay 831 to relay 'A' 815 if the storage device 870 is the same voltage 832 as the main circuit voltage 813, 801 voltage. If the storage device 870 is at a different voltage than the main circuit voltage 813, 801, the voltage 832 may be provided 833 directly to the lamp 802, such as in a loss of power 801 condition.

Relay control communication can be facilitated via LAN 817, 826 and/or wireless 816 such as WiFi or Bluetooth. The relays 815, 820 may be solid state variable voltage outputting devices to dim the lights 802, 803 together or independently, for example. Dimming may be controlled to achieve a specified lumen as set using, for example, a dimmer 812 and/or from the system's remote computer control (the workflow engine) 841 to lower light lumens as a function of a clinical protocol and/or energy management 842. The disclosed system's logic may be beneficially activated to minimize energy use from either lighting or HVAC subject to the clinical protocol requirements.

Figure 9:
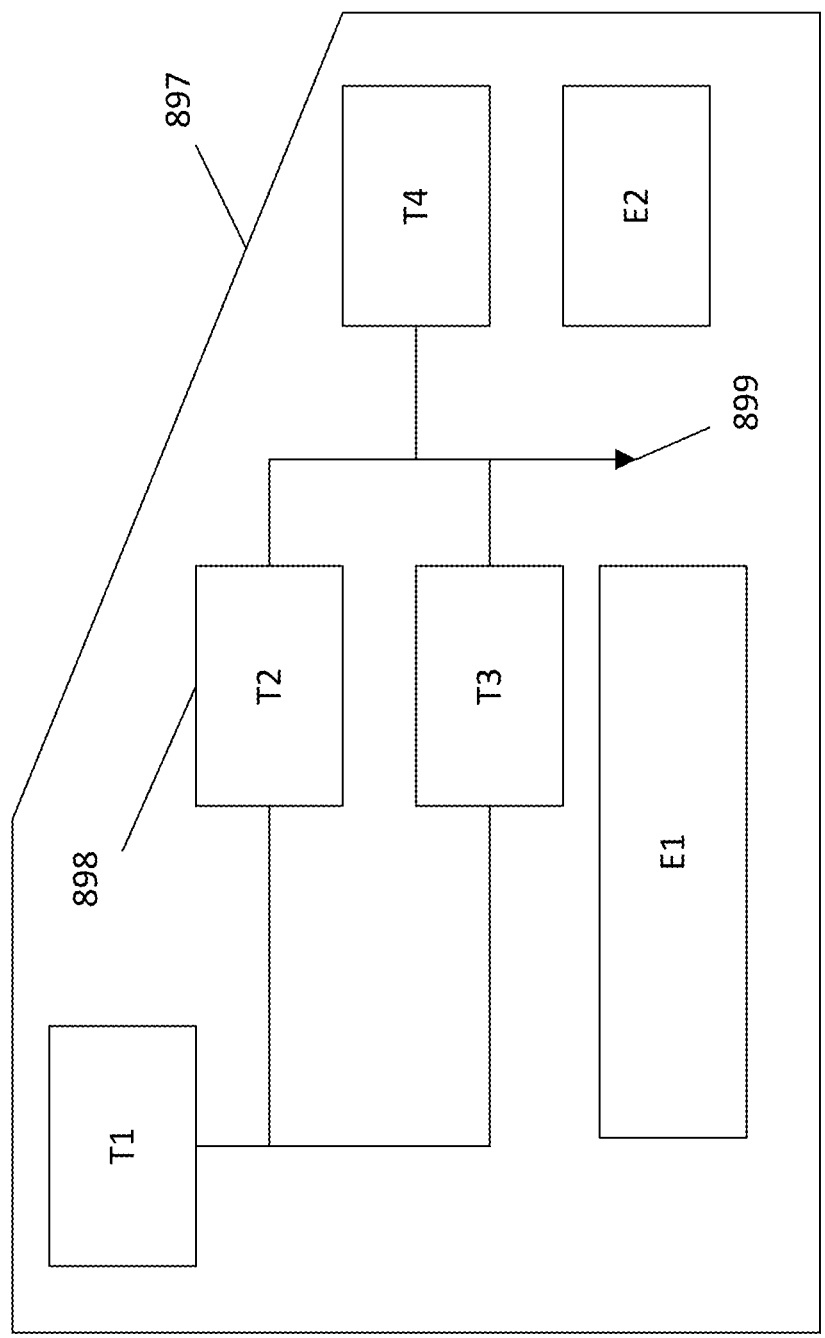
FIG. 9 shows an example clinical protocol including a plurality of tasks for a monitored and controlled clinical and light interaction.

As an illustrative example, shown in FIG. 9, a clinical protocol 897 has a plurality of tasks for a monitored and controlled clinical and light interaction. In the example of FIG. 9, the protocol proceeds through Task T1, then executes Tasks T2 and T3 in parallel and then performs Task T4. For example, Task T1 may be identifying a patient put in a bed for an evening sleep protocol; Task T2 is preparation of the bed for safe sleep by the patient; and Task T3 monitors the patient with respect to determining whether the patient is getting out of bed (e.g., not to Task T2 at 898). Task T4 is to lower lighting to off or night light level, per care orders. Energy is denoted as E1, E2 which are given as lumen levels. In the protocol, if the patient attempts to exit the bed at Task T3, the light control varies the illumination level from E1 to E2 in an attempt to wake the patient out of a disoriented state at 899.

Figure 10:
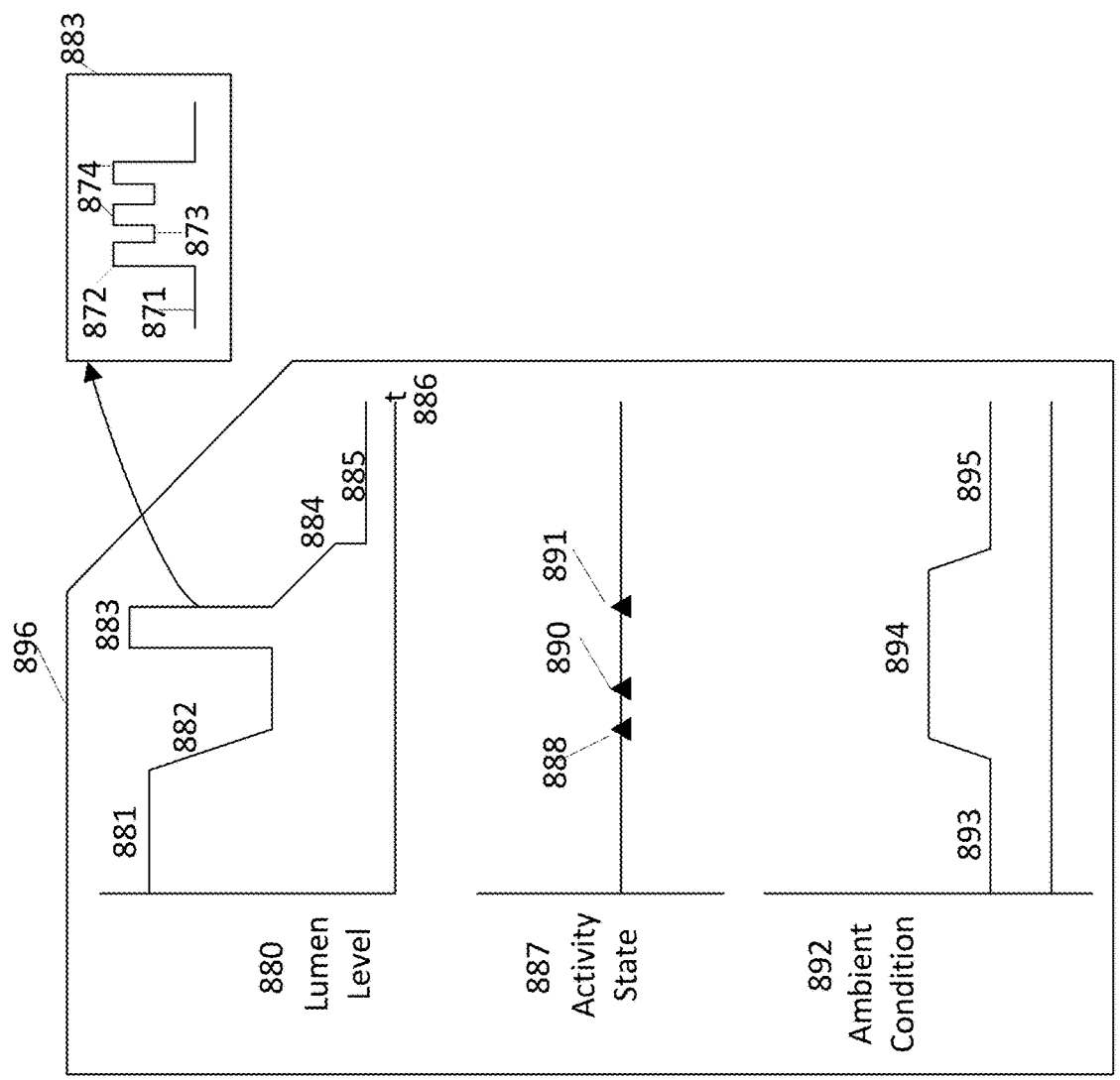
FIG. 10 illustrates an example ambient control which manages lumen level as a function of activity state and ambient condition of a room.

An ambient control 896 is, in the example of FIG. 10, managing lumen level 880 as a function of activity state 887 and ambient condition 892 of the room. Ambient condition 892 includes one or more non-clinical aspects such as room light level that influence lumen level 880 in a room. For example, window light also adds to the monitored space's light. As shown in the example of FIG. 10, the lumen level 880 is specified to be at a level 881 as a function of time 886. As the sun shines into the monitored space, the exterior light changes from a low level, such as in the early morning 893 to a higher level 894 through sunrise and the morning. The lamp provided lumens ramp down 882, thus saving energy. As the sun sets and exterior light lowers 895, the clinical protocol calls for lower light, such as for sleep, and the lumens are caused to be reduced 884 to a low level such as either "off" or "night light level" 885.

If the patient attempts to exit the monitored bed, the Doppler sensor 830 detects the accompanying motion 888, 898 and triggers a varying light pattern 883, 899 to make patient aware of the request to not leave the bed. As called out in the expanded view of the light level 883, shown in the example of FIG. 10, the light level is ramped from its scheduled level 871 to a high level 872 and then oscillated, for example, between two levels 872 to 873 for a frequency 874. When the detected condition comes back into protocol 890, the lighting is returned to schedule 871. At a further time of day 886, the lumens are reduced to a low level 885 at certain sleep level 891.

The example system 800, shown in FIG. 8, enables energy management as well as lighting and/or HVAC control according to a protocol, defined as a purposed series of tasks. For example, light level is used herein to illustrate an example interaction with activities in the monitored space. It can be appreciated that temperature and humidity may also and/or instead be controlled as a function of activity in a monitored space.

In an illustrative example of a duality of objective between activity in the monitored space and energy cost benefiting from the example system 800, a clinical rule implemented by the system 800 specifies a low lumen level during certain hours to enable a sleep protocol. The lumen reference signal 841 is sent to the room controller 812 which functions as a dimmer in the example. Actual room lumens are sensed 805 by a device which may be mounted in a lamp 802, 803 or other sensing system 843 or in the local controller (which may be stand alone or integrated into the lamp) 812 or a dedicated device with visibility to a room 809. Communication 806 from the lumen sensor 805 may be wired or via wireless such as Wi-Fi or Bluetooth 841. The light is lowered according to the protocol. However, at a particular time, one or more the system's sensors 830, 843 may detect motion and determine, probabilistically with respect to the implemented protocol(s), that, for example, the patient is getting out of bed or is attempting to get out of bed in contradiction to the care protocol. If, in the example protocol, the patient is not to get out of bed (e.g., as a measure against the risk of falling, etc.), the controller may raise the room lights or pattern the lights between lumen levels to provide a visible indication that is direct feedback to the patient to remind or caution the patient that his or her actions are not in accordance with the protocol. Alternatively or in addition, if the situation is not one in which lights are a component of the clinical process control, lumens of light in the room 809 can be increased so as to provide a light level in the room 809 to reduce a risk of falls or bumps by the patient in the room 809.

While certain illustrative examples facilitate use of utilities to impact the patient safety domain, it can be appreciated that use of light level and light patterns as facilitated by a controller, a protocol(s), adjustable light level, HVAC and/or activity sensors (e.g., in the lamp and/or hidden from view, such as above a ceiling 807 in a space 836 above the room's plenum 808, etc.) form a system 800 useful to control and facilitate activity in the illuminated and/or controlled space.

Power management combined with energy storage helps ensure that the sensing system and lamps function when needed. For example, the Doppler device 830 is powered directly 834 and/or from 832 a light 803 or battery 870 or any combination thereof.

Communication of an occupancy sensor (e.g. Doppler) directly to the protocol or capacity or energy controllers, or room controller 812 may be via LAN 835 or wireless 837. Other sensor(s) 843 may beneficially also be so configured.

The Doppler sensing device 830 may be located integral to the lamp 802 or above the space's ceiling 807. A benefit to placement of the Doppler sensor 830 in the room's 809 plenum 808 is that clean architectural lines, more flexible room usage, and physical protection are afforded. The plenum height 836 facilitates Doppler sensor 830 adjustment length 836 above the ceiling 807 and can be maintained, for example, by an adjustable bracket 875 that affixes the device 830 to the suspended ceiling channels 876. The bracket 875 may be height- and orientation-adjusted to achieve an angle and clearance, for example. The bracket 875 may be suspended itself and/or enable attachment to structure(s), for example.

In some examples, the light fixtures are of a variety of types. FIG. 11 shows an example table of lights, controls, and relays such as relay A 815, relay B 820, and relay C 825 from the example of FIG. 8. As shown in the example table of FIG. 11, lights can be provided as LED 855 and/or fluorescent 854 light in the room 809. Power 801 can be switched 850, switched with a dimmer 851, controlled with a microprocessor based drive 852, and/or powered via a LAN 853 as appropriate for the type of lamp. A variable voltage and/or variable frequency controlled lamp uses appropriate supporting electronics, for example.

Lamps may be incandescent, LED, fluorescent, etc. If bulb(s) and fixture(s) are fluorescent 854 without dimming capability, the lamp is either switched 850 or powered 860 via relay A 815 with light relay D 831 also energized. Dimmable lamps such as incandescent or LED or in some designs fluorescent may be dimmed 851. The controller 852 may switch on/off or provide variable voltage 861 to fluorescent and/or LED lights via relay A 815, B 820, and/or C 825. An LED 862 may be powered from a LAN 853. Other combinations of the lights and sensors may be powered in a like schema.

Figure 12:
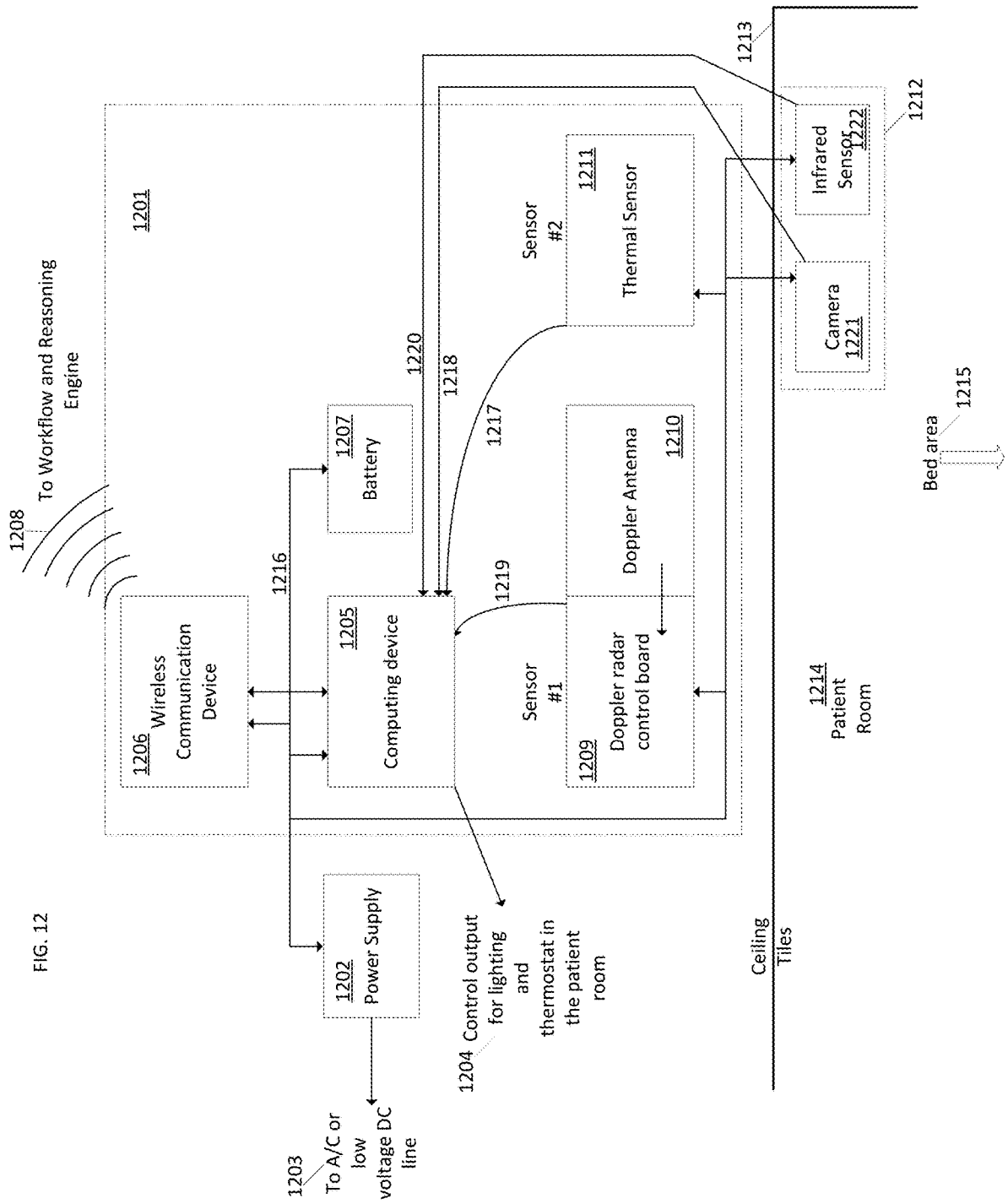
FIG. 12 illustrates physical elements of an example sensing component.

FIG. 12 illustrates physical elements of an example sensing component 1201. The component 1201 may be installed above a ceiling tile 1213 of a hospital and/or other healthcare facility room 1214 and may include one or more sensors 1212 located in other parts of the hospital room 1214 such as within a visible area of the room 1214. Elements of the sensing component 1201 include one or more sensors 1209, 1211, 1221, 1222; a computing device 1205; a wireless communication device 1206; and, optionally, a battery 1207. All sensors 1209, 1211, 1221, 1222 are connected 1217-1220 to the computing device 125, and all or most components may be connected 1216 to a source of power 1202.

The sensors 1209, 1211, 1221, 1222 can detect signs of occupancy in a patient room 1214. One or more sensors 1209, 1211, 1221, 1222 of the same or different methodology may be incorporated into a single instance of the sensing component 1201. Examples of sensing methodologies include Doppler radar (which incorporates an antenna 1210 and an electronic control board 1209, for example), thermal sensing 1211, a video camera 1221, and/or an infrared sensor 1222.

The computing device 1205 manages the operation of the sensors 1209, 1211, 1221, 1222 and evaluates data from one or more sensors 1209, 1211, 1221, 1222 to determine a current occupancy state of the room 1214. The computing device 1205 also communicates with a workflow and reasoning engine 1208 through a wireless communication (e.g., WiFi, Bluetooth, etc.) link 1206, and may also communicate with and/or control the room's environmental systems through a control output 1204, for example.

The sensing component 1201 requires electrical power which may be supplied via an external source 1202 and/or an internal battery 1207. The external power supply 1202 may be derived from either standard A/C power (e.g., ~120 or 240 volts) or low-voltage DC power (e.g., 12-24 volts) 1203.

As shown in the example of FIG. 12 and described further below, various sensing technologies which may be incorporated into example sensing component 1201. At least one such sensor 1209, 1211, 1221, 1222 is required for operation, and the component 1201 may incorporate multiple instances of the same or different type of sensor to monitor each individual room 1214.

Doppler radar technology 1209, 1210 permits detection of occupancy in a room 1214 under a variety of conditions ranging from ambulation (large motion) of a patient across the room 1214 to very small motions corresponding to the respiration of a sleeping patient under a blanket. This sensing technology 1209, 1210 can be positioned in a way that is not visible from within the room 1214 (such as above ceiling tiles 1213), and generates a one-dimensional signal which does not violate patient privacy concerns since the signal cannot be used to identify a specific individual. The Doppler control board 1209 generates an electronic pulse which is transmitted through the antenna 1210 and broadcast to the patient room 1214. Items or occupants in the patient room 1214 reflect the radar pulse back to the antenna 1210, which then transmits any return pulse back to the control board 1209. The control board 1209 compares a profile of the return pulse to profile(s) of previous pulse(s) to identify change(s) in configuration of the room 1214 which indicate motion of objects in the room 1214. The control board 1209 then transmits a low-voltage analog output 1219 to the computing device 1205. The magnitude of the analog output 1219 corresponds to a degree of motion detected within the sensing range of the specific combination of control board 1209 and antenna 120. The range of distances over which the Doppler sensor 1209, 1210 operates (e.g., in terms of minimum and maximum distance from object to antenna) can be controlled by a pulse width generated by the control board 1209, for example.

In some configurations, multiple Doppler radar sensors 1209, 1210 may be integrated into a single sensing component 1201. For example, a radar with a high-gain, directional antenna (able to detect very low-level motion such as respiration) may be positioned over a bed area 1215 of the room 1214 to help ensure high accuracy in detecting a patient sleeping under a blanket. A second sensor with a wide-angle antenna may be set up to monitor other areas of the room 1214 for larger motions, such as that of a patient moving about the room 1214. A level of motion produced by a patient sitting in a chair is in between the extremes of sleeping and walking about, and can be captured by one of the two radar sensors, for example.

Thermal imaging 1211 is another sensing technology which may be incorporated into the example sensing component 1201. This type of sensor 1211 measures a temperature and/or heat profile within the room 1214, and a resulting signal 1217 can be analyzed by the computing device 1205 to assess whether or not the room 1214 is occupied. Thermal imaging does not require a patient to be in motion (or respirating) for detection. This type of sensor 1211 may be located such that it is not visible to a patient, such as positioned above the ceiling tiles 1213 in the room 1214.

Additional sensing technologies which may be incorporated include a video camera 1221 and infrared (IR) imaging 1222. Unlike Doppler radar and thermal imaging, these types of sensors 1221, 1222 should be positioned within the physical patient room 1214 and below any ceiling tiles 1213. The video camera 1221 can be used to capture moving or still images to be transmitted 1218 to the computing device 1205; these images can then be analyzed to identify the presence of humans within the room 1214. IR imaging 1222 relies on a transmitted and reflected pulse similar to the method of Doppler radar, but the IR pulse does not pass through ceiling tiles 1213. The IR sensor 1222 generates and transmits an infrared pulse into the room 1214, evaluates the reflections generated by any objects in the room 1214, and compares a series of reflections to identify configuration changes related to the motion of objects in the room 1214. Information is transmitted 1220 from the IR sensor 1222 to the computing device 1205 to be analyzed by the computing device 1205 to identify the presence of people in the room 1214.

As shown in the example of FIG. 12, an output 1204 to control lighting and thermostat levels within the patient room 1214 may be provided. The output 1204 is generated by the computing device 1205 based on a current level of occupancy in the room 1214 (per analysis of data from the sensor(s) 1209, 1211, 1221, and/or 1222 connected to the device 1205) and parameters transmitted to the computing device 1205 from the workflow and reasoning engine 1208, for example. Examples of such uses include automatically setting a thermostat to a comfortable level as soon as the workflow engine 1208 determines that the room 1214 has been assigned to a new patient (e.g., to allow temperature to adjust in advance of the patient's arrival), and adjusting lighting in the room 1214 to correspond to the room's occupancy state, etc.

Figure 13:
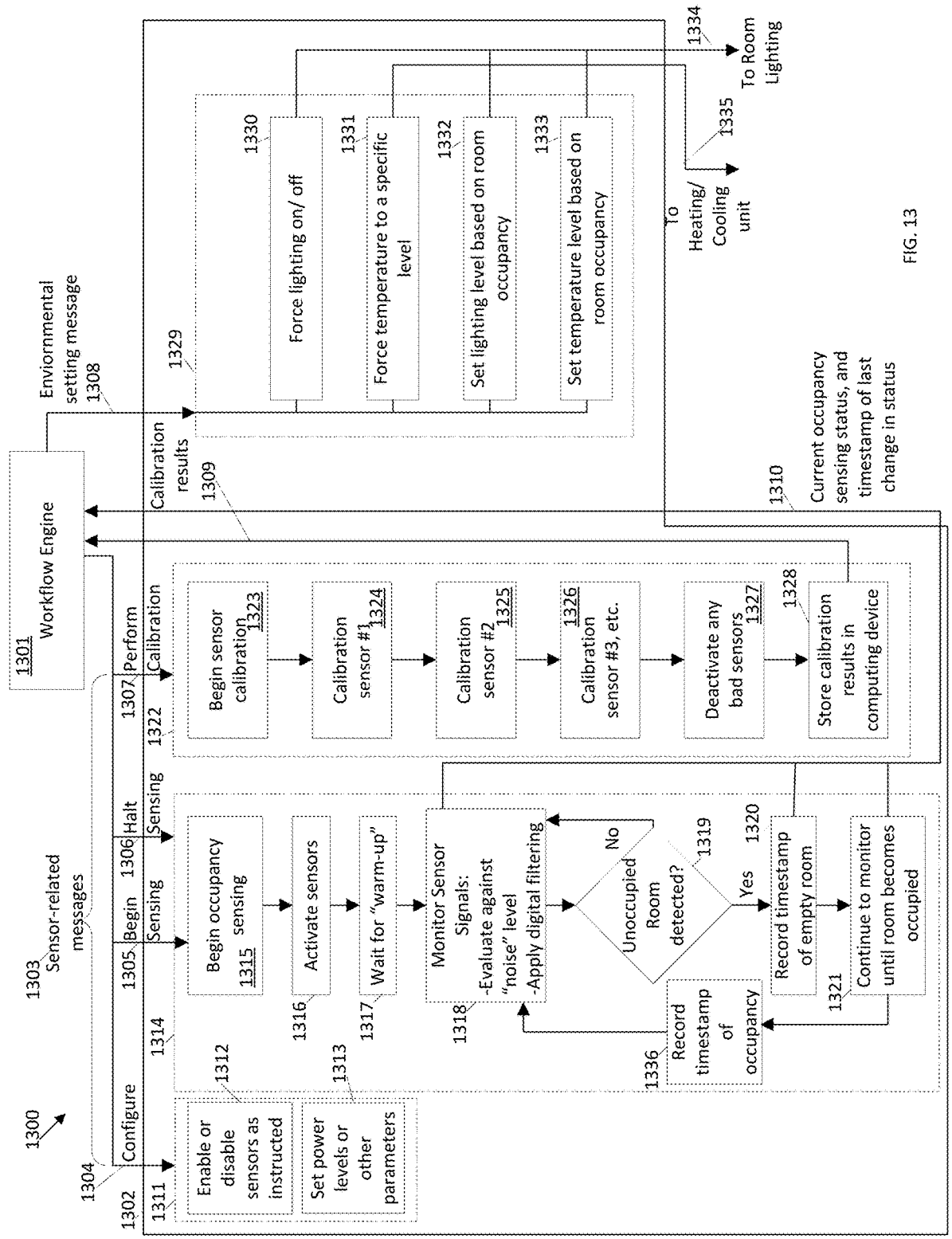
FIG. 13 is a flow diagram of an example operation of an example sensing component.

FIG. 13 is a flow diagram of an example operation 1300 of an example sensing component 1302. The example flow diagram describes general capabilities of the sensing component 1302 and its interaction with a workflow engine 1301. The actions shown within the flow diagram of FIG. 13 represent computations and signal analysis performed by a computing device within the sensing component 1302. The workflow engine 1301 may guide the operation of the sensing component 1302 through a number of control messages 1303, 1308 and in turn may receive messages 1309, 1310 indicating the status or current results of various operations.

A control message 1304 instructs the sensing component 1302 to configure its one or more occupancy sensors as specified in the configuration message 1304. A range of actions 1311 may include enabling and/or disabling specific sensors 1312, and setting output power levels for individual sensors and/or other parameters 1313, for example.

Another control message 1305 instructs the sensing component 1302 to initiate occupancy sensing for a specific room or bed for which the sensing component 1302 has been installed to monitor. The control message 1305 initiates a sequence of events 1314 to begin occupancy sensing 1315 with activation of a desired configuration of sensors 1316 and possibly waiting for a "warm-up" period 1317 during which sensor signals are expected to stabilize. Once the sensing device(s) are considered ready to proceed, the sensing component 1302 proceeds to continuously monitor the signals received from the active sensors 1318. Signals are monitored to determine whether the signals provided by the sensors to the computing device indicate that the room is either occupied or unoccupied 1319. As part of this process, each sensor's signal may be compared against a "noise" threshold or other calibrated value, and digital filtering may be employed to reduce a likelihood of false results, for example.

As monitoring proceeds, the computing device of the sensing component 1302 evaluates whether current conditions indicate that the room is likely unoccupied 1319. If not (e.g., indicating that occupancy is currently detected), monitoring proceeds unchanged 1318. However, if the "unoccupied room" condition is detected (e.g., indicating no motion or no indication of human presence or activity), a timestamp of this state is recorded 1320. The sensing component 1302 then continues to monitor the occupancy state of the room 1321. If such monitoring later indicates that the room has become occupied, a timestamp for this event is recorded 1336, and the sensing component 1302 returns to monitoring for the room to become unoccupied 1318.

The sensing component 1302 is able to provide messages 1310 to the workflow engine 1301 indicating the current occupancy state of the room (e.g., occupied/unoccupied) and the timestamp or duration reflecting the time at which the last change in state occurred. For example, such a message might indicate that the room is currently unoccupied and has remained so for a given time period (e.g., 31 minutes).

In certain examples, the occupancy monitoring algorithm 1318 contains digital filtering to permit short-duration changes in state to be ignored and not change the output of the device. For instance, if a room has been unoccupied for a sizeable amount of time (~30 minutes) but then there is a brief period of motion (such as someone opening the door, looking inside the room and then closing the door without entering), the digital filter can ignore the motion and continue to report that the room is unoccupied. However, if the motion persists for a longer period (such as a person actually entering and remaining in the room), the digital filter reports that the room is now occupied. The digital filter can be configured as to an amount and duration of motion which can be ignored.

A further control message 1306 instructs the sensing component 1302 to halt occupancy sensing. If the computing device is currently running the occupancy sensing algorithm 1314, this halt message 1306 causes the sensor's computing device to stop the sensing process and deactivate all sensors.

Another type of control message 1308 from the workflow engine 1301 may instruct the sensing component 1302 to set or affect various environmental controls and/or other hospital operational systems 1329 for the patient room. If the sensing component 1302 includes or is in communication with a lighting control for room lighting 1334, control messages 1329 can include setting lighting to a specific value 1330 (e.g., on, off, particular lumens value, etc.), setting lighting based on the last known occupancy level of the room 1332, etc. If the sensing component 1302 includes or is in communication with a temperature control for a heating/cooling unit in the room 1335 (such as a thermostat setting, etc.), control messages can include setting temperature to a specific value 1331, setting the temperature based on the last known occupancy level of the room 1333 (possibly in context with time of day), etc.

As illustrated in the example of FIG. 13, a control message 1307 instructs the sensing component 1302 to perform a calibration 1322. At block 1323, sensor calibration begins. At block 1324, a first sensor is calibrated, followed by calibration of a second sensor at block 1325, calibration of a third sensor at block 1326, etc., until all available sensors have been calibrated (e.g., a "noise" threshold or other calibrated value for sensor data comparison, etc.). At block 1327, any "bad" sensors failing their calibration 1324-1326 are deactivated. In some examples, improperly responding or "bad" sensors can be flagged for maintenance, re-calibration, etc. At block 1328, calibration results are stored in the sensing component's computing device.

Figure 14:
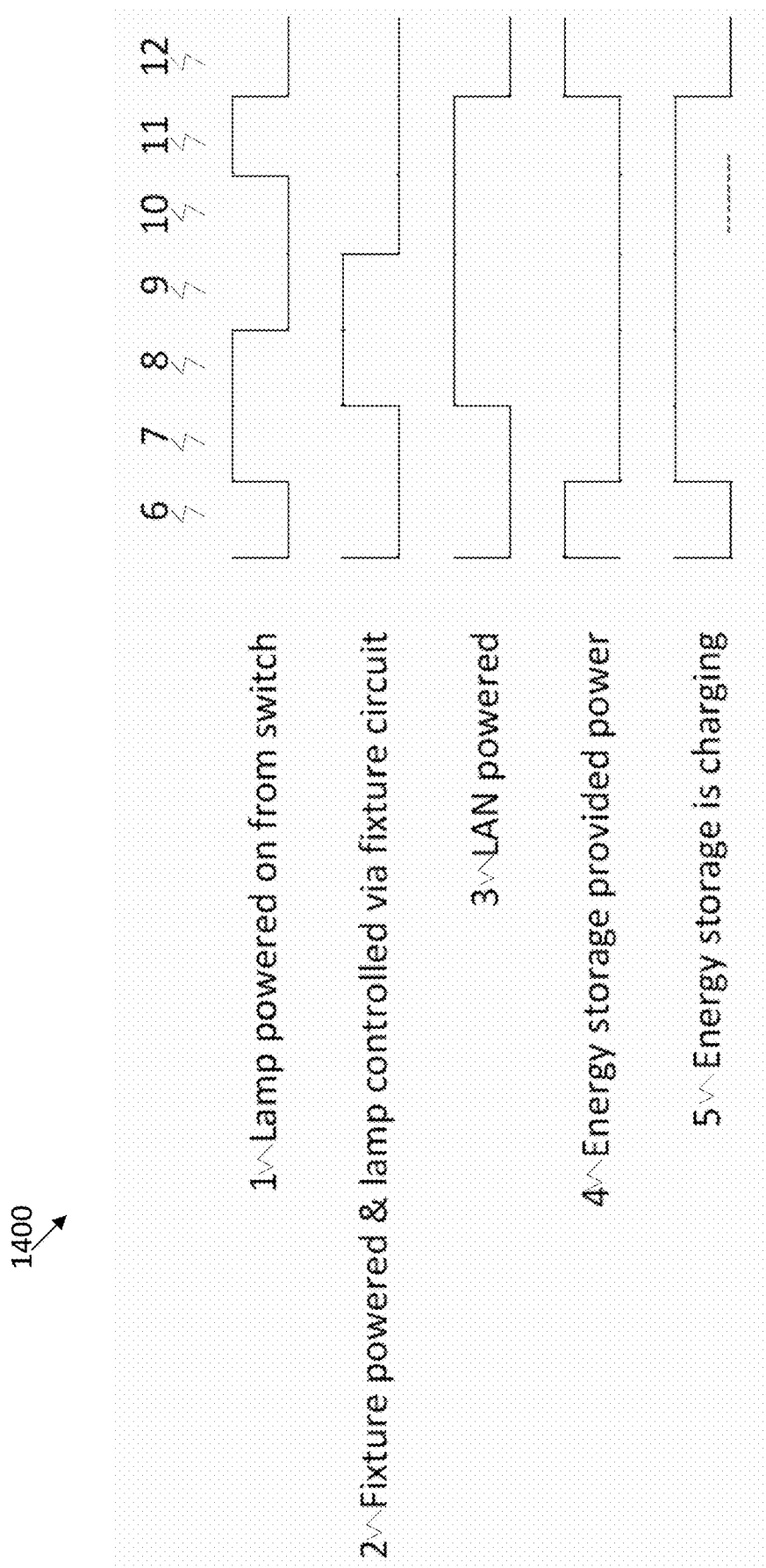
FIG. 14 illustrates an example Boolean logic for power management with respect to the presently disclosed technology.

FIG. 14 illustrates an example Boolean logic for power management with respect to the presently disclosed technology. Certain examples include a power management control 1400 which enables power management and sensing system to be retrofit into legacy hospitals, which by tradition have powered lamp circuits from a manually toggled switch. The example of FIG. 14 shows five energy sources for a room occupancy system which harvests power from a lamp circuit. The harvesting system 1400 beneficially eliminates a need to create new power circuits and/or conduits, ceiling removal, room contamination, extended room outages, and associated costs thereof, for example.

Certain examples enable four energy provisions: a lamp powered 1 from a switched location(s) which is/are on or off; a constantly powered fixture 2 which may use original wiring but bypasses an associated toggle switch and controls voltage to the lamp via a relay or solid state circuit on the lamp fixture or adjacent control box; a local area network powered sensing system 3 whose energy draw may be gated as shown or continuous; and an energy storage device 4, such as a battery, whose charge/discharge is also controlled. The energy storage 5 may charge from the switched lamp circuit 1, the powered fixture or direct wired circuit 2, the LAN 3 and, optionally, solar energy harvesting and is actively controlled as a function of storage charge state and available charging power, for example.

There are seven energy states that are controlled by the example system 1400. A first energy state 6 depicts no switched lamp power 1, no constant powered 2, no LAN powered 3, but energy storage power 4 provided. A second energy state 7 depicts toggled lamp power 1 and energy storage charging 5 (to the extent that the energy storage requires charging at the time), but no constant power 2 or LAN power 3. A third energy state 8 includes available power from a toggled lamp switch1, a "fully on" circuit 2, and LAN power 3, with energy storage charging 5 (if needed) but no energy storage provided power 4. Control logic in the system 1400 uses a higher voltage, for example, 120 VAC lighting circuit 2, rather than the LAN power 3 in state 8 based on demand for power and/or other usage criterion, for example.

A fourth energy state 9 enables system power from either a fully energized fixture 2 or LAN 3 when a switched fixture 1 is toggled off. Charging is allowed from either the fully on circuit 2 or LAN 3, with a preference in the example to the line voltage of the fixture 2.

A fifth energy state 10 is LAN powered 3 and charging 5. The charging rate is beneficially lowered by the system 1400 so as to limit the current attained from LAN power 3, and, if the energy storage is sufficient with respect to the pattern of line voltage harvesting, the system 1400 suspends charging when running solely on LAN power 3, unless the energy storage level is below a dynamically set point (e.g., a low battery level necessitating charging).

A sixth energy state 11 includes toggled switch-lamp power 1 or LAN power 3, where the system 1400 benefi cially first harvests the available line power 1. While the energy storage is not providing power 4 in the energy state 11, the energy storage is being charged 5. A seventh energy state 12 is power by energy storage discharge 5 in the absence of line voltage 1, 2, 3.

Dual Doppler Sensor Examples

As described above, certain examples provide a new Doppler motion sensor that, rather than being a commodity security product, is constructed and configured to monitor a patient's vital signs such as respiration and heartbeat. However, a single Doppler motion sensor can only detect human motion in a small area, due to the limited field of view of its high directional antenna to sense subtle human motion. Certain examples provide a Dual Doppler occupancy sensing system that integrates two Doppler sensors to detect 1) a stationary person in a small area of interest, such as a hospital bed, and 2) normal motion in a large area, such as a person sitting or walking in a hospital room. In certain examples, two identical Doppler sensors are integrated with a first Doppler antenna's main lobe pointing downward and a second Doppler antenna's main lobe facing sideways. The first Doppler sensor is for monitoring patient activity in bed, and the first Doppler sensor facing downward is referred to herein as the "primary sensor". The second Doppler sensor is for monitoring patient activity in the room and is referred to herein as the "secondary sensor".

The integration of two motion sensors enables the combined system to detect both subtle motion, such as respiration motion, and also typical hospital activities, such as walking in the room. The second Doppler sensor can be low-cost and still provide a larger coverage area and better performance without increasing much installation and hardware cost. Using two Doppler radars, the combined sensor can detect a stationary person in a targeted area, as well as human motion in a larger monitored area.

Figure 15:
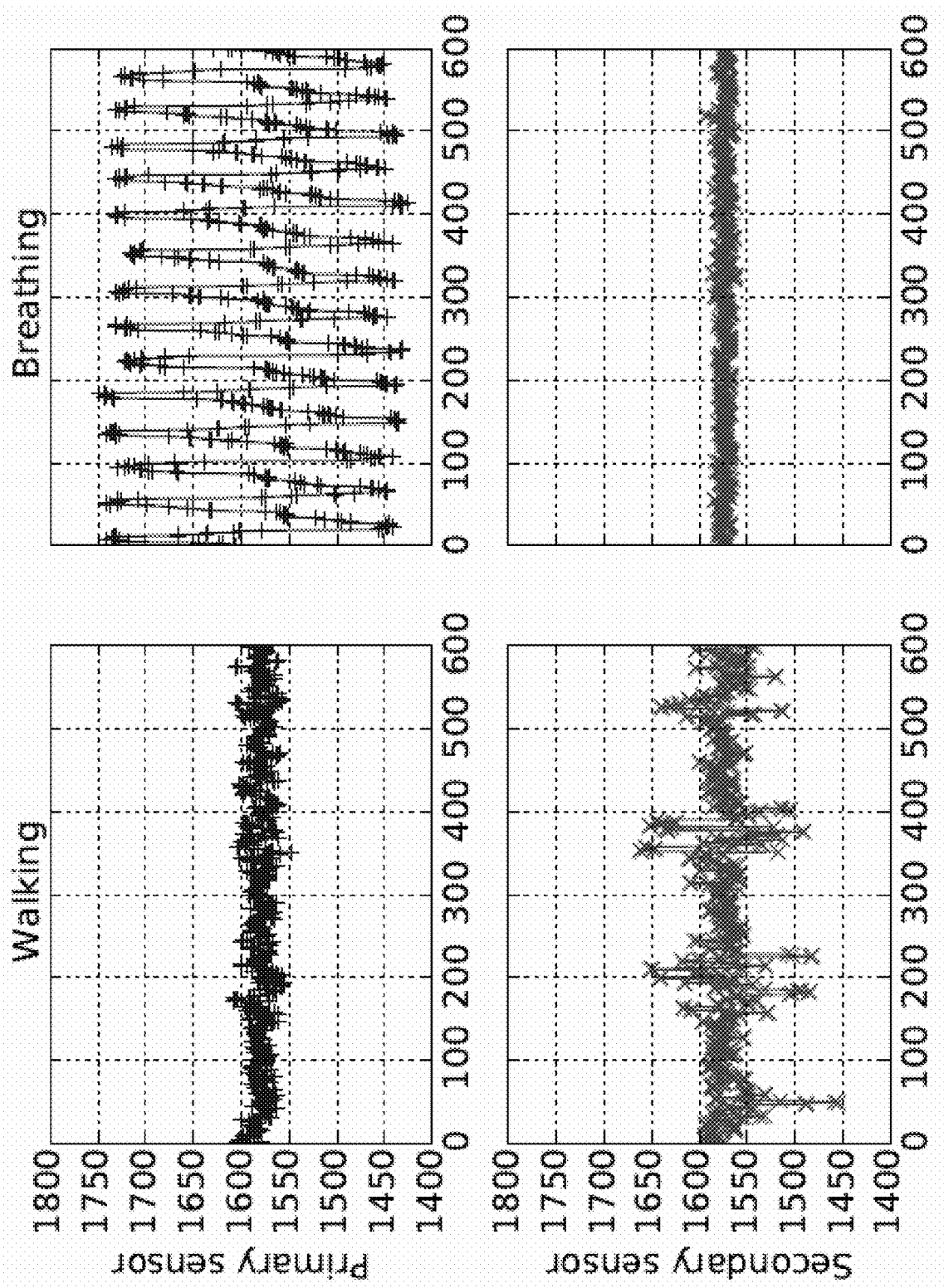
FIG. 15 illustrates example Doppler signals from two sensors when a person is walking into a room and breathing in bed.
Figure 16:
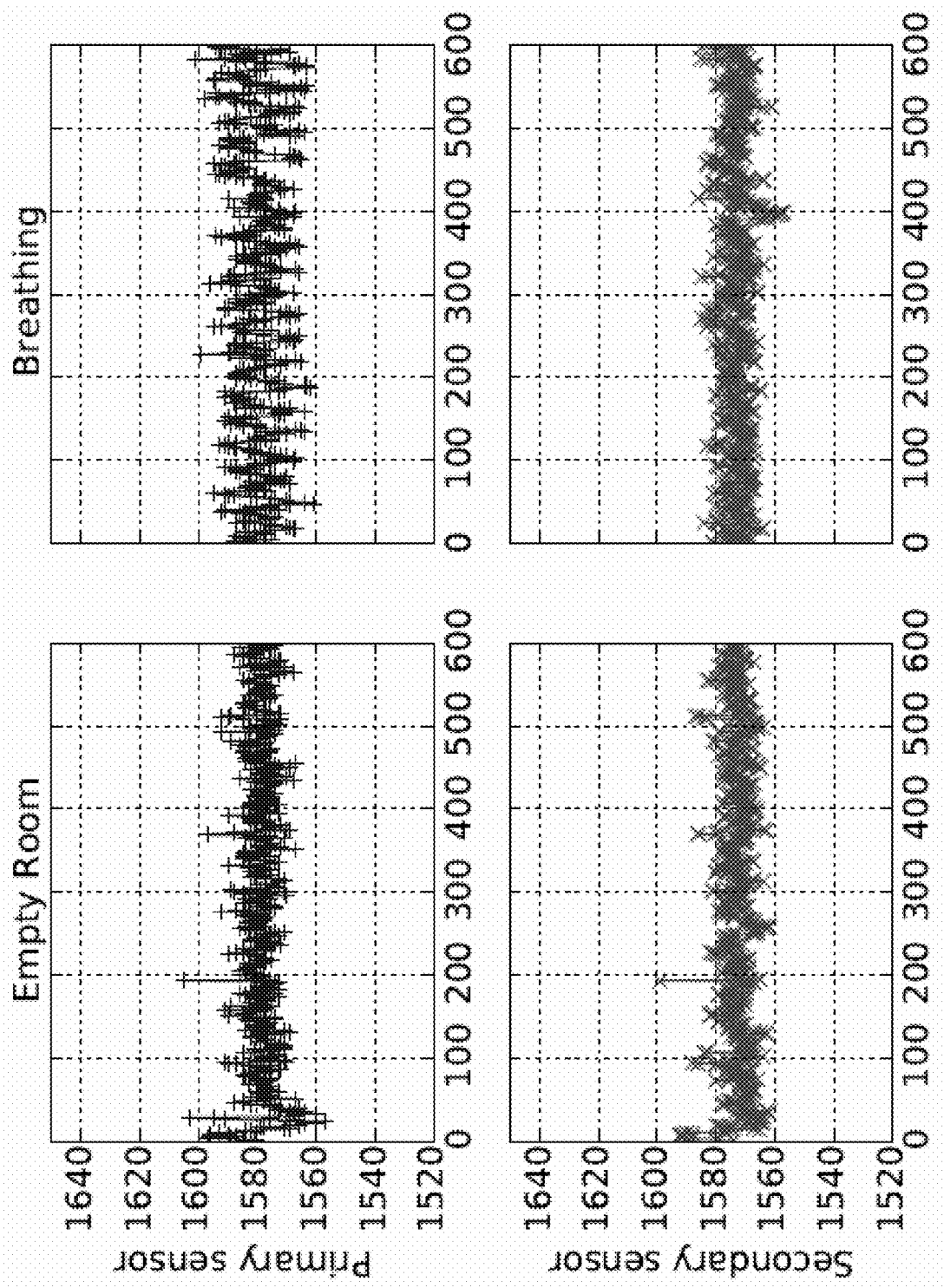
FIG. 16 shows example Doppler signal data for an empty room as compared to a room in which a patient is breathing.

FIG. 15 illustrates example Doppler signals from two sensors when a person is walking into a room and breathing in bed. FIG. 16 shows example Doppler signal data for an empty room as compared to a room in which a patient is breathing.

Certain examples provide a finite state machine algorithm for noise reduction in conjunction with the dual Doppler sensor. An example algorithm includes a sequential detection algorithm using time and frequency domain information. A data fusion algorithm can also be provided. Thus, certain examples provide a combined algorithm including: 1) a person detection algorithm using both a variance of a Doppler signal in the time domain and power spectrum density in the frequency domain; 2) a logic algorithm to combine detection results from multiple motion sensors; and 3) a finite state machine (FSM) algorithm for noise reduction on state transition (e.g., reduce incorrect transition from an occupied state to an empty state, or vice versa, due to noisy measurements.

First, variance of Doppler signal during a time window (such as 25 seconds) is used as a metric in the time domain to measure a variation caused by human motion. A baseline variance without any human motion can be quantified by collecting data offline when no person is present in a room. The range of the baseline variance can be calculated from many empty-room tests and represented as: $(\theta_0, \theta_1)$. Then, during an online test period, a variance of Doppler signal for each time window can be compared with the baseline variance. If the online variance is larger than an upper bound of the baseline variance range $(\theta_1)$, then human motion is detected at that time window. If the online variance is smaller than the lower bound of the baseline range $(\theta_0)$, no human presence is detected at that time. If the variance is in the range of ($\theta_0$, $\theta_1$), a power spectrum density (PSD) is calculated and serves as another detection metric.

Figure 17:
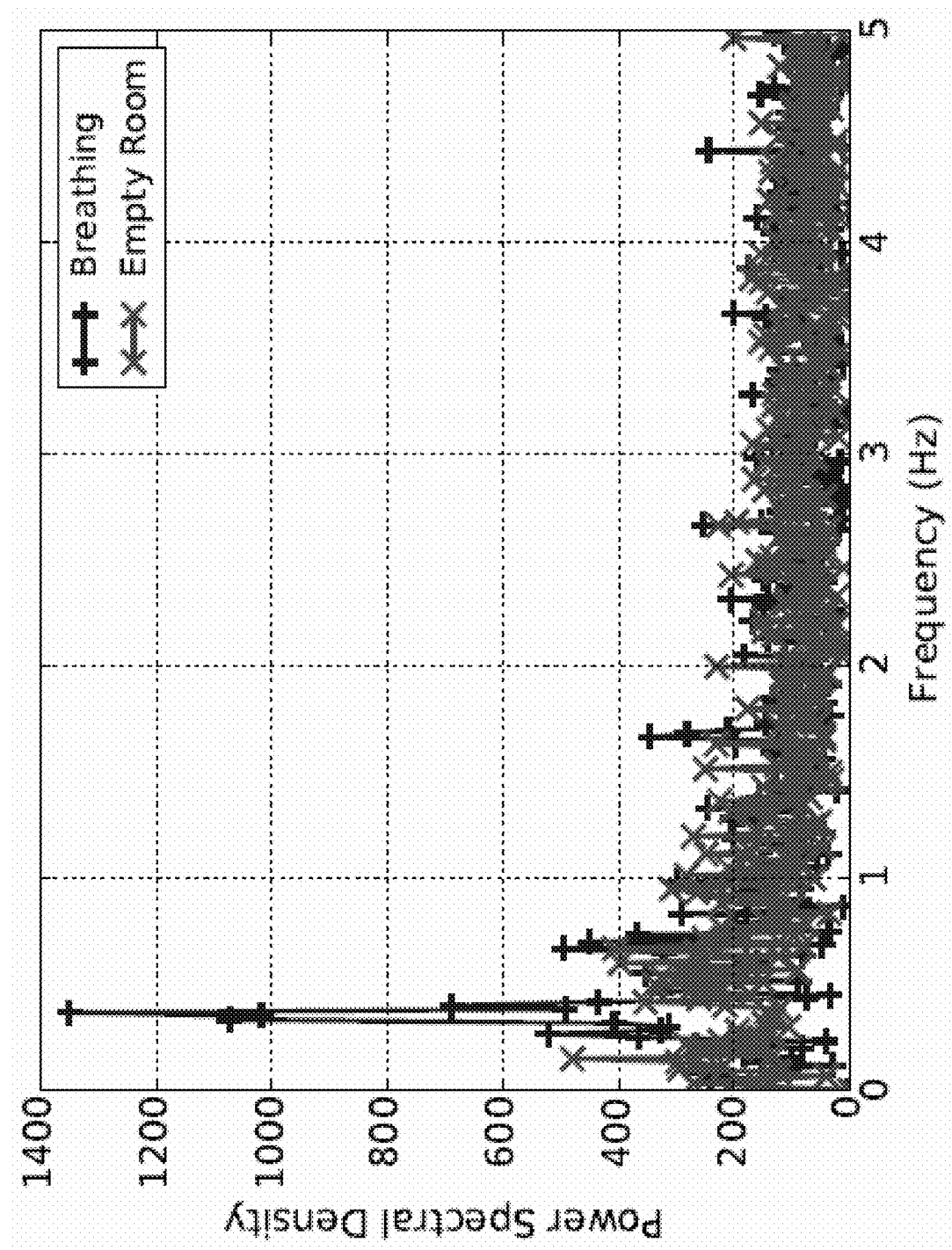
FIG. 17 shows an example of measured power spectral density versus frequency to identify a periodic respiration pattern captured by a sensor.

In certain examples, PSD is used as a second metric since respiration motion can be hard to detect if the motion is orthogonal to a direction of Doppler radiofrequency (RF) propagation. As shown in the example of FIG. 17, a periodic respiration pattern can be captured by the primary sensor, but the variation is not as clear as in the example of FIG. 15. In the example, the variance of the Doppler signal is 57.9, slightly greater than an empty room signal (e.g., the noise floor, 33.7). However, if PSDs are computed, the signal with respiration has a PSD peak at the frequency of the respiration rate, while the empty room signal has no such peak, as shown in the example of FIG. 17. If estimated PSD matches PSD of a normal respiration motion well (for example, estimated PSD has a unique and high peak at the typical respiration rate of an adult, which is 12-20 breathes per minute), then a stationary person is detected. If estimated PSD does not match a typical respiration rate, then no detection result is made at this time window, and the next time window is added with current time window to repeat the above procedure. Thus, this detection algorithm is a novel sequential detection method combining both time domain information and frequency domain information to detect presence or absence of a patient in an area.

Second, a logic OR operator is used to fuse the detection result from each sensor together. After the sequential detection algorithm is run individually on each motion sensor in each time window, the detection results from both motion sensors serve as inputs to a logic OR unit to produce the final detection result. If any one of the motion sensors detects human presence, then the final detection is positive (room occupied). If all sensors detect no human presence, then the final result is negative (room empty).

Figure 18:
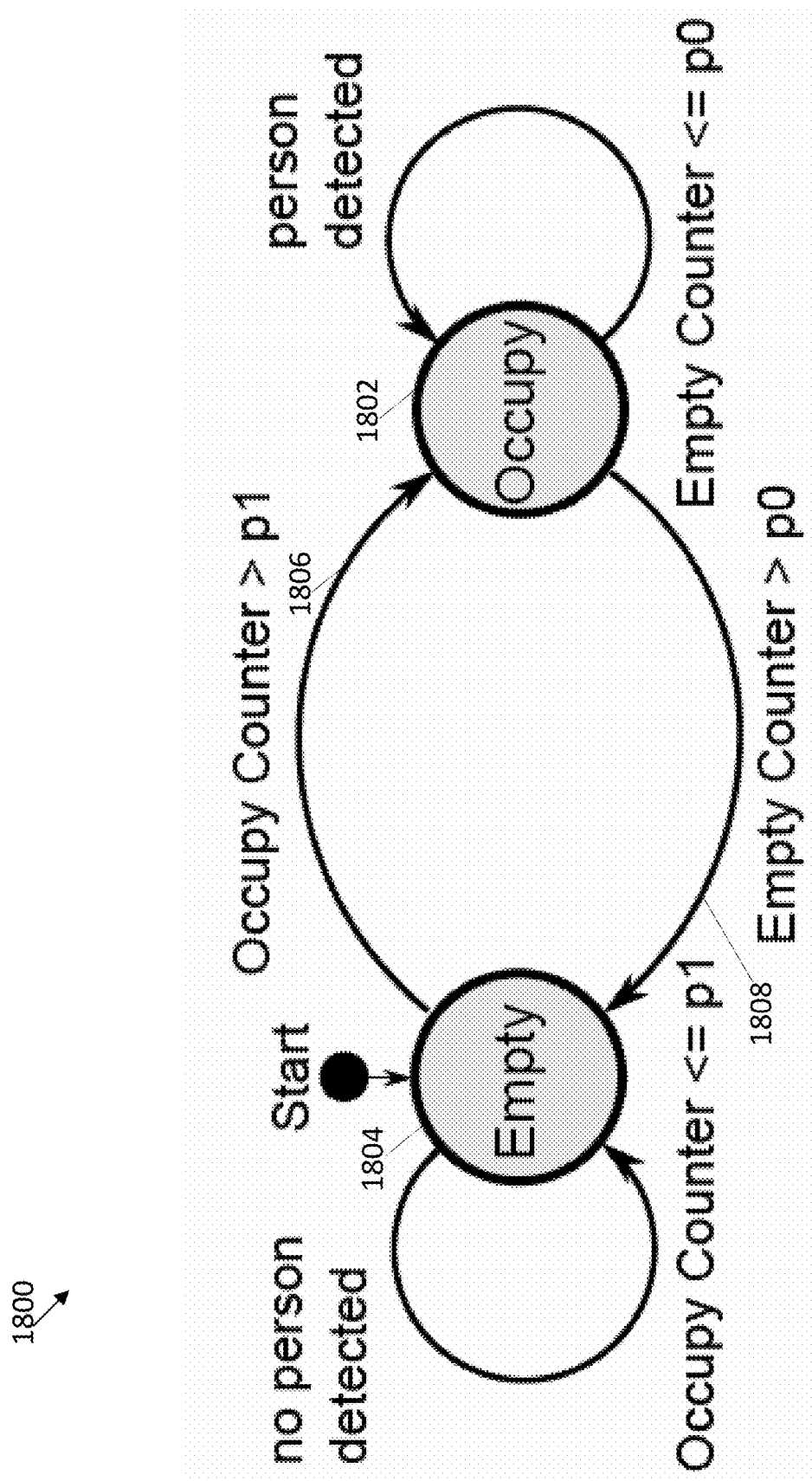
FIG. 18 illustrates a finite state machine showing state transitions from an occupied state to an empty state and from the empty state to the occupied state.

Finally, the system also includes a finite state machine algorithm to filter out noise and false detection result to make the occupancy detection system more robust. The final detection result from the logic OR unit is fed into a finite state machine algorithm to decide if the room state remains the same or the opposite. As illustrated in FIG. 18, two counters, an occupy counter ($\alpha_1$) and an empty counter ($\alpha_0$), are used in an example state machine 1800 for a state transition from an occupied state 1802 to an empty state 1804 and from the empty state 1804 to the occupied state 1802. If the occupancy detection result is positive (human presence detected), then the occupy counter $\alpha_1$ increases by one, and the empty counter $\alpha_0$ is cleared to zero. If no human presence is detected, $\alpha_0$ increases one count, and $\alpha_1$ is set to zero. If the occupy counter $\alpha_1$ is above a pre-defined threshold $p_1$, a state transition 1806 is triggered from the empty state to the occupied state. The same rule applies to a state transition 1808 from the occupied to the empty state using the empty counter $\alpha_0$ (the empty counter $\alpha_0$ is above a pre-defined threshold $p_0$). Note that the pre-defined counter threshold values $p_0$ and $p_1$ for $\alpha_0$ and $\alpha_1$ can be different and can be set according to specific application needs, such as a system latency requirement, an amount of noise in measurements, etc.

Example Discharge-Sensing Logic

Figure 19:
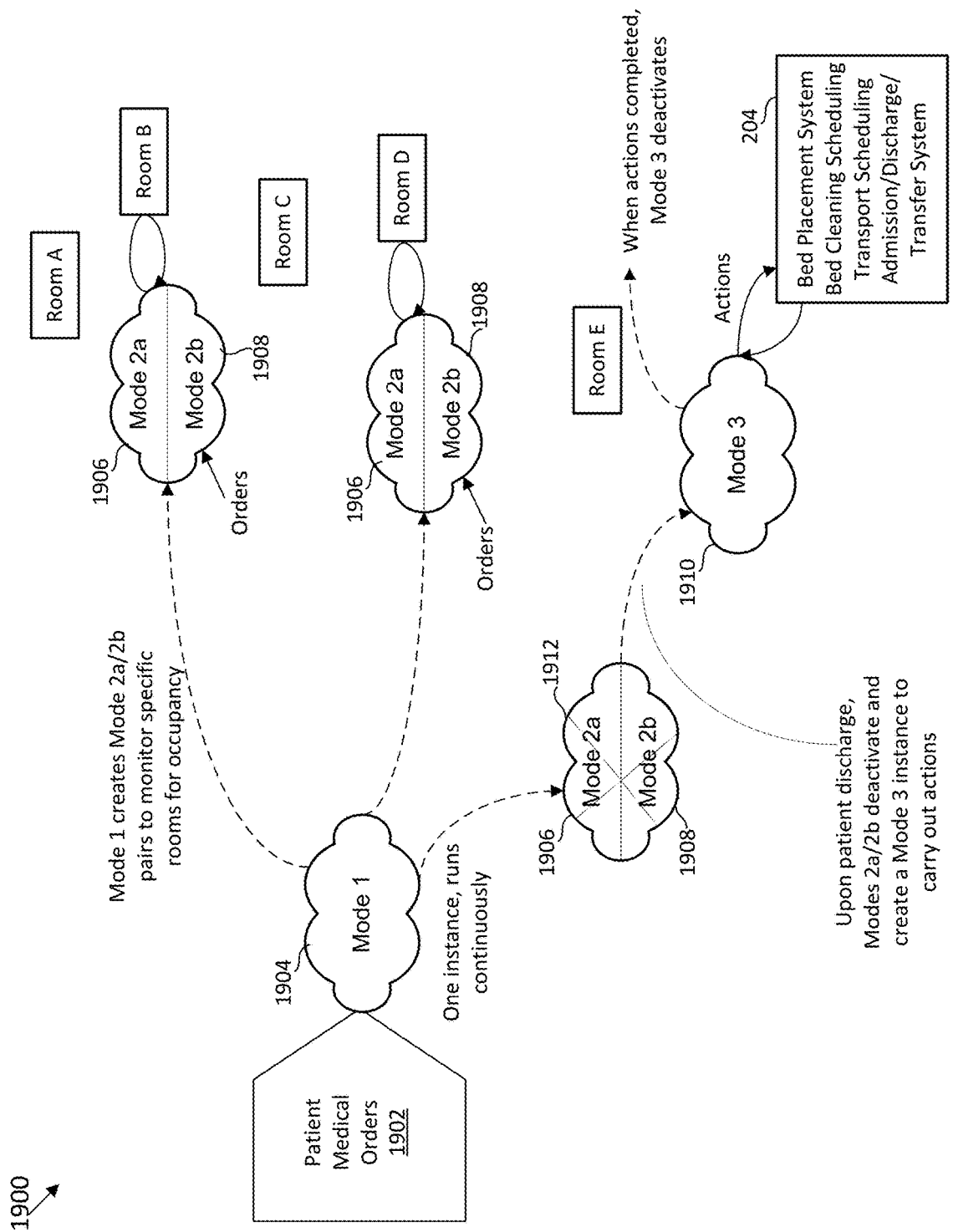
FIG. 19 illustrates logic, parameters and resulting actions involved in a discharge-sensing operation across various modes according to the presently disclosed technology.

Logic, parameters and resulting actions involved in a discharge-sensing operation are illustrated with respect to the example of FIG. 19. As shown in the example of FIG. 19, discharge-sensing logic 1900 has four modes of operation—Mode 1 1904, Mode 2a 1906, Mode 2b 1908, and Mode 3 1910. All modes 1904, 1906, 1908, 1910 can run continuously and in parallel (as implemented on one or more networked computing devices, for example) in order to process and monitor multiple patients simultaneously. The modes 1904, 1906, 1908, 1910 and their interactions are described briefly below. Following the brief description, a more detailed description of logic and parameters for each mode 1904, 1906, 1908, 1910 is provided. Several examples (e.g., scenarios) are provided to demonstrate potential outcomes for a hospital and/or other healthcare facility with and without sensing mechanisms and methodologies as disclosed herein.

Mode 1 1904 logic continuously scans inpatient medical orders to identify patients who are likely to be discharged in the near term (e.g., less than six hours). If a candidate patient is found, the Mode 1 1904 logic spawns a pair of Mode 2a 1906 and 2b 1908 logic instances dedicated to monitoring that patient's occupancy (Mode 2a) and order status (Mode 2b). In the example of FIG. 19, only one instance of Mode 1 logic is required and is implemented on a central server.

Mode 2a 1906 and Mode 2b 1908 logic monitor a specific patient's room occupancy and any additional medical orders to determine if and when the patient has discharged. Mode 2a 1906 monitors occupancy while Mode 2b 1908 monitors medical orders for the same patient. Thus, Mode 2a 1906 and 2b 1908 represent a pair of "companion" instances dedicated to a specific patient.

If an instance of Mode 2a 1906 determines that its patient has been discharged, Mode 2a 1906 invokes an instance of Mode 3 logic 1910. The Mode 2a 1906 instance is then de-activated or eliminated and also causes its companion Mode 2b 1908 instance to be eliminated 1912. If an instance of Mode 2b 1908 determines (as described further below) that occupancy sensing is no longer relevant for that patient, Mode 2b 1908 causes itself and its companion Mode 2a 1906 to be eliminated.

In certain examples, Mode 2b logic 1908 is implemented on a central server capable of handling the number of Mode 2b instances 1908 running in parallel (evaluating separate patients), while instances of Mode 2a logic 1906 may either be built into each individual occupancy sensor installed in patient rooms or implemented on a central server (evaluating separate patients in parallel), for example.

Mode 3 logic 1910 triggers, monitors and guides various physical and electronic actions upon the discharge of a specific patient. The specific Mode 3 instance 1910 is eliminated once such activities are completed or fulfilled.

More specifically, Mode 1 1904 discharge-sensing logic is used to identify inpatients who, based on their electronic medical orders, appear to be likely candidates for discharge from the hospital in the near future (e.g., within a predetermined historical threshold of minutes such as 30 minutes, less than 60 minutes, etc.). In Mode 1 1904, data requirements include a continuously updated electronic list of inpatients and their bed/room assignments, a continuously updated electronic flow of inpatient medical orders covering (at least) discharge orders, surgical orders (including case date, if scheduled) and orders for interventional or diagnostic imaging, for example. Other useful inputs (if available) include orders for any in-hospital procedures or processes which are indicated to be completed prior to the patient's discharge and would require the patient to leave their room. Examples of such orders include physical therapy sessions at an in-house department.

Parameters and factors to set up the system in Mode 1 1904 include a list of order types which the discharge-monitoring system should evaluate. For example, at some hospitals a "pending" discharge order indicates that patient departure is likely farther than 24 hours away, while a "confirmed" discharge order indicates that departure is likely within 24 hours. In this case, the system should be configured to scan for confirmed orders only. A list of inpatient beds and rooms within scope for discharge monitoring and/or a list of any patient types or other factors which would cause a patient to be excluded from monitoring can also be evaluated and factor in to the discharge monitoring.

In certain examples, upon receipt of each new medical order, the order is evaluated to determine whether refers to a patient currently assigned to an in-scope bed and room. If the order refers to a patient currently assigned to an in-scope (e.g., monitored) bed and room and the order type falls within a configured set of discharge-relevant orders, then all outstanding orders for that patient are gathered. If the patient now has a discharge order (e.g., of a type consistent with near-term discharge, as described above), and does not have any other orders that require a procedure or therapy (e.g., which must take place in the hospital, prior to discharge, and at a location other than the patient's room, etc.), then an instance of Mode 2 logic 1906, 1908 is created to monitor the patient's bed and room for occupancy. If these conditions are not met, the Mode 1 logic 1904 ignores these orders and returns to scanning incoming orders.

When these conditions regarding an in-scope patient with a discharge-relevant order and no other hospital procedure/ therapy order are met, a paired instance of Mode 2a 1906 and 2b 1908 logic is created and activated to monitor a specific patient, bed and room. Any number of paired Mode 2a/2b instances 1906/1908 can be created.

For Mode 2a logic 1906, a specific patient's bed and room are monitored for occupancy, and Mode 3 logic 1910 is activated when the room is determined to be empty for a suitable period of time. For Mode 2a logic 1906, data includes an electronic identification of the patient, bed and room to be monitored. Parameters and factors for Mode 2a 1906 include an unoccupied-room time limit, such as 30 minutes, indicating a threshold at which a room remaining unoccupied should be considered to represent departure (discharge) of the patient. Parameters/factors also include an interval to aggregate Doppler sensor data into a single evaluation of motion in the room, such as 15 seconds. In some examples, software filtering can then be applied to each 15 second result. A threshold for the aggregated Doppler output that differentiates motion (occupancy) from no-motion (empty room) is also provided and/or otherwise set (e.g., by a user, by a monitoring program, automatically based on historical data, based on measurement, etc.). The threshold value may be specific to an individual sensor and room location. Additional controls for a digital filter can be provided in Mode 2a 1906 such as a number of successive "no-motion" signals which must be observed to switch the recorded state of the room from occupied to empty.

In Mode 2a 1906, a state of the room to "occupied" is initialized (e.g., set to a default value). Additionally, a variable "time occupancy was last observed" is set to the current time, and the Doppler sensor is activated. If the Doppler sensor has a warm-up delay, Mode 2a logic 1906 waits until the sensor indicates it is ready for use. Then, a motion-sensing and digital filtering algorithm is executed for software filtering. Then, a motion evaluation is acquired from the Doppler sensor. Acquiring a motion evaluation involves aggregating for a set amount of time, as indicated in parameters. The motion signal is sent to the software filter and results are assessed. If the software filter indicates that the room is currently occupied, "time occupancy was last observed" is set to the current time, and Mode 2a 2906 returns to continue monitoring the room.

Otherwise, if the filter indicates the room is currently unoccupied), the current time is compared to the value of "time occupancy was last observed". If the interval between these two times is less than an unoccupied room time limit (e.g. 30 minutes), then Mode 2a return to continue monitoring the room). Otherwise, if the interval between the times indicates that the room has been unoccupied longer than the indicated time limit, an instance of Mode 3 logic 1910 is created, and the instance of Mode 2a 1906 and its companion Mode 2b logic 1908 are removed. In certain examples, the cycle described above may continue indefinitely unless the room becomes empty for a suitable amount of time or the Mode 2a 1906 is interrupted by its companion Mode 2b instance 1908 as described further below. When conditions described in Mode 2a 1906 are met, an instance of Mode 3 logic 1910 is created and activated to carry out discharge-related activities for the specific monitored patient.

In certain examples, Mode 2b logic 1908 includes monitoring a specific patient's new medical orders for any changes which indicate the patient is no longer a likely candidate for near-term discharge. In Mode 2b 1908, a current set of electronic medical orders relevant to the specific patient and a flow of any additional (e.g., incremental, etc.) electronic medical orders for that patient are processed. As with Mode 1 1904, a list of order types that should be evaluated and factor(s) that would cause a patient to become excluded from monitoring are used to set up the Mode 2b 1908 and system for monitoring. In Mode 2b 1908, incoming order flow for the patient (if any; it is expected that no new orders will be received for a discharging patient) is monitored.

When a new order is received, the new order is compared to a list of orders which would preclude a patient from being a likely discharge candidate (e.g., as described for Mode 1 1904, this list may include revised discharge orders of a type or timeline which indicate the patient is now unlikely to discharge within the next 24 hours, etc.). If the new order precludes the patient from near-term discharge, then the companion Mode 2a 1906 instance is de-activated, and this Mode 2b instance 1908 is de-activated as well. If the new order does not preclude the patient from near-term discharge, then the new order is added to the set of existing orders, and Mode 2b 1908 continues to monitor new medical orders for the patient. This cycle of monitoring and processing may continue indefinitely unless a suitable order is received or the Mode 2b 1908 is interrupted by its companion Mode 2a instance 1906 as described above (e.g., due to the patient having departed the room).

In certain examples, Mode 3 1910 activates and guides physical and digital actions involving a particular bed and room upon detection of a patient discharge in order to expedite patient flow through the hospital. In Mode 3 1910, a bed and room of the discharged/departed patient are monitored along with a set of electronic medical orders relevant to the discharging patient. Mode 3 1910 involves access to an electronic inpatient bed placement (e.g., request) system and identification of those bed requests which are compatible with the bed and room of the discharged patient (e.g., placing the new patient into this location would be an acceptable match). Access to systems including an electronic bed board, admission/discharge/ transfer system, and scheduling for bed cleaning and patient transport is facilitated in Mode 3 1910.

In Mode 3 1910, parameters and factors to set up the system include configuration (of Mode 3 and/or of the bed request system, for example) to identify outstanding bed requests which are a suitable "fit" for the recently discharged bed. Mode 3 1910 operates according to one or more guidelines to prioritize patients for placement if more than one patient is a suitable fit for the bed (for example, "longest waiting" or "surgical first", etc.). Configuration and operation of the scheduling systems are described above to permit control signals to be sent by Mode 3 1910.

In Mode 3 1910, a message is sent to the electronic bed board indicating that the discharged bed is now unoccupied (but not yet cleaned). Then, a message is sent to the admission/discharge/transfer system indicating that the previous patient has now been discharged. Mode 3 1910 then sends a message to the bed cleaning system to schedule the discharged bed and room for cleaning. In Mode 3 1910, the list of outstanding inpatient bed placement needs is scanned to identify one or more bed placement needs (e.g., patients) that are compatible with the discharged bed. If a compatible placement need is found (including any placements definitively assigned to the discharged room), then Mode 3 1910 sends a message to the bed-cleaning system asking the cleaning to be expedited since there is a patient waiting to occupy this bed. Mode 3 1910 waits for a message from the bed cleaning system indicating that the room is ready for occupancy. If the electronic bed board still indicates that the newly-discharged (and now clean) bed is unassigned, then Mode 3 1910 re-scans the list of outstanding inpatient bed placement needs (e.g., requests) for placement needs that are compatible with and/or assigned to the newly-discharge bed. A rescan is executed because some requests may have been fulfilled and others added to the list during the time of bed cleaning.

If any compatible requests are found, then one request is selected by Mode 3 1910 based on the hospital's prioritization guidelines. Mode 3 1910 sends a message to the bed-placement system indicating that the request will be fulfilled by the bed which is being monitored by Mode 3 1910. In some examples, Mode 3 1910 waits for human confirmation of patient placement into the bed. Once confirmation is received, Mode 3 1910 sends a message to the electronic bed board and admission/discharge/transfer system indicating the new patient assignment. Additionally, Mode 3 1910 sends a message to the transport scheduling system requesting that the new patient be transported from his or her current location to the bed. Following the request for transfer, the instance of Mode 3 1910 can be deactivated, as the interaction of the occupancy sensing system with the particular bed and room have been concluded until the instance of Mode 3 1910 is re-activated by Mode 1 1904 as described above. Thus, Mode 3 1910 schedules and monitors bed cleaning staff, placement of a new patient into the available bed, and schedule transport staff to convey the patient to the bed, for example.

Figure 20:
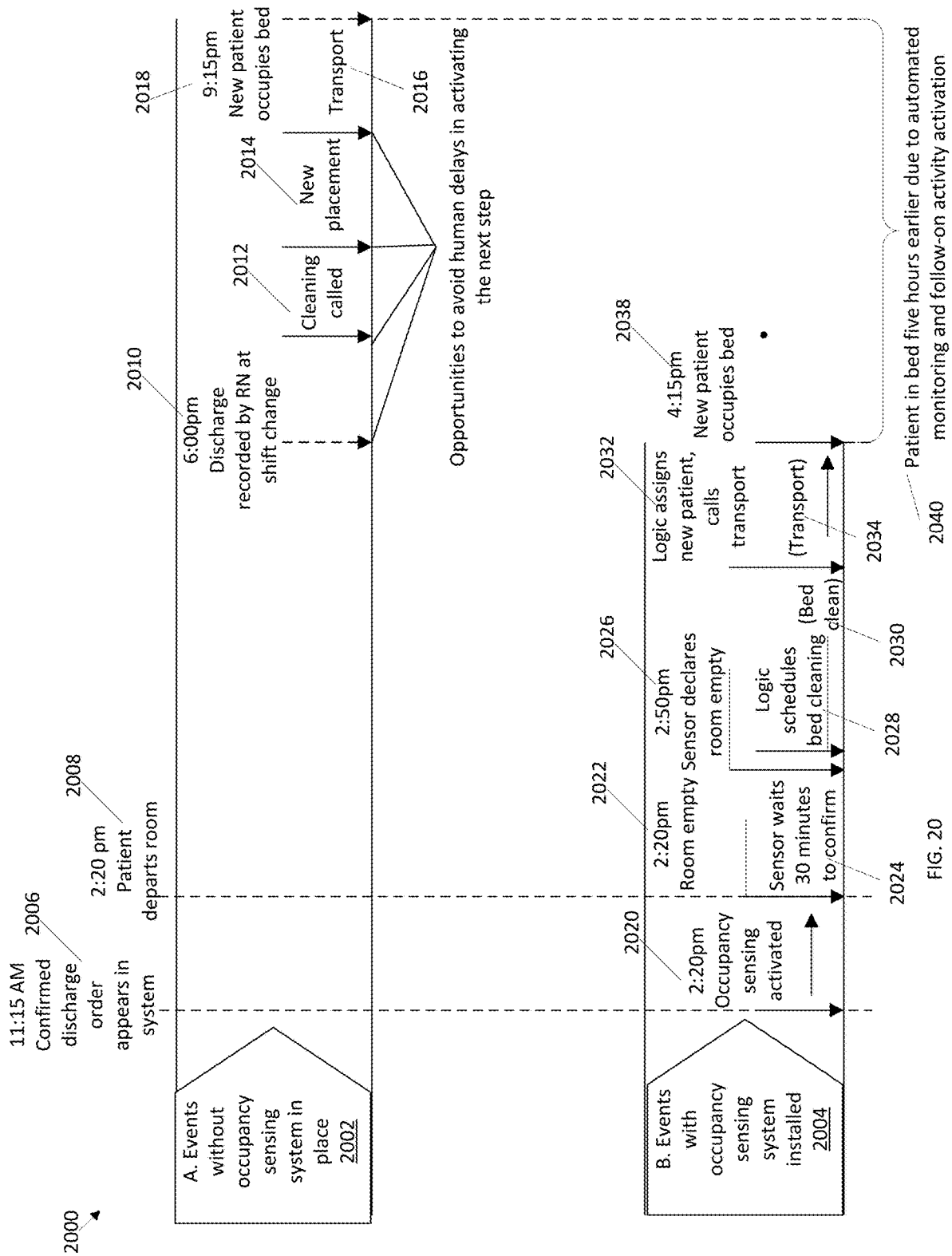
FIG. 20 illustrates potential outcomes and delays occurring with and without an occupancy sensing system in place according to the presently disclosed technology.

Some examples illustrating operation of the mode logic of FIG. 19 are described with respect to FIG. 20. FIG. 20 illustrates potential outcomes and delays occurring with 2004 and without 2002 an occupancy sensing system in place. FIG. 20 represents a timeline of events 2000 from left to right, beginning with a discharge order being written at 11:15 am 2006 and the corresponding patient departing his or her room at 2:20 pm 2008. These two events 2006, 2008 are the same in both scenarios 2002, 2004, as the events happen independently of the sensing system (if present). All events to the right represent events driven by the presence 2004 or absence 2002 of an occupancy sensing system.

In scenario A 2002, the hospital does not have an occupancy sensing system installed in the room (and does not have the associated logic modes connecting occupancy status to activities such as bed cleaning, placement and patient transport). In this example, the patient's discharge is not recorded in electronic systems until start of the next shift at 6 pm 2010, several hours after actual departure from the room 2008. Such a time lapse is not unusual, especially when discharge information is entered in batch mode at start or end of shift, for example. An additional delay occurs before the bed cleaning staff is called 2012 to clean the room. Once the room has been cleaned, there is a delay before the bed-placement staff is aware that the room is clean and that a suitable placement can be made into the room 2014. After more delay, the new placement 2014 is made and transport 2016 is called. Finally, at 9:15 pm the new patient occupies the bed 2018.

In scenario B 2004, the hospital has an occupancy sensing system installed in the room and also has the associated logic modes with connections to orders and physical systems. In this example, the appearance of a discharge order at 11:15 am 2006 triggers the main logic (Mode 1 1904) to activate the occupancy-sensing system 2020 for that patient room (controlled by instances of logic Modes 2a 1906 and 2b 1908). At 2:20 pm, logic Mode 2a 1906 detects that the room is now unoccupied 2022 but waits for a given threshold amount of time 2024 (in this example, 30 minutes) to elapse before declaring the room to be unoccupied with confidence at 2:50 pm 2026. An instance of Mode 3 1910 is now activated which schedules the room for expedited cleaning 2028 (since there is a suitable bed placement waiting for this bed) and monitors until the cleaning system indicates that the room is ready to accept a new patient 2030. The logic of Mode 3 1910 then assigns a waiting placement to the bed and schedules the patient transport system to move the patient to the new room 2032, 2034. At 4:15 pm, the patient occupies the room 2038, five hours earlier than in the previous scenario 2040 (scenario A).

Thus, certain examples provide an important benefit of a physical occupancy sensor, which reliably identifies discharge within a short time frame of the patient's actual departure. Additionally, benefit is obtained from automated coordination between the sensing system and other hospital systems (e.g., cleaning, assignment, transport, etc.) following discharge, which helps mitigate a possibility of additional delays due to "human in the loop." Examples of such delays are intervals between bed cleaning and assignment, when a human bed placement operator may not become aware for some time that a suitable room is newly ready for use.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory.

Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Figure 21:
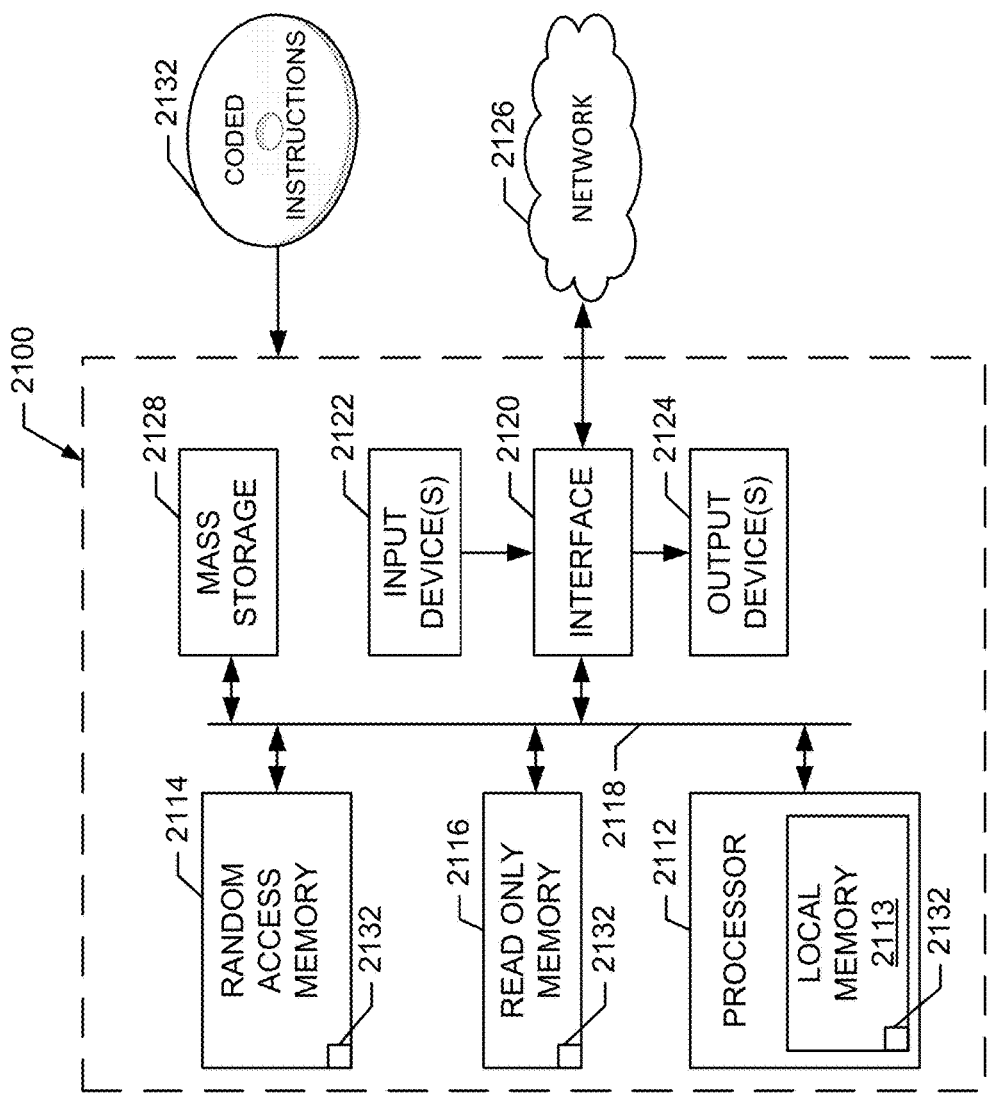
FIG. 21 is a block diagram of an example processor platform capable of executing instructions to implement the example systems and methods of FIGS. 1-20.

FIG. 21 is a block diagram of an example processor platform 2100 capable of executing instructions to implement the example systems and methods of FIGS. 1-20. The processor platform 2100 can be, for example, a server, a personal computer, a mobile device (e.g., a cell phone, a smart phone, a tablet such as an IPAD™), a personal digital assistant (PDA), an Internet appliance, or any other type of computing device.

The processor platform 2100 of the illustrated example includes a processor 2112. Processor 2112 of the illustrated example is hardware. For example, processor 2112 can be implemented by one or more integrated circuits, logic circuits, microprocessors or controllers from any desired family or manufacturer.

Processor 2112 of the illustrated example includes a local memory 2113 (e.g., a cache). Processor 2112 of the illustrated example is in communication with a main memory including a volatile memory 2114 and a non-volatile memory 2116 via a bus 2118. Volatile memory 2114 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2116 can be implemented by flash memory and/or any other desired type of memory device. Access to main memory 2114, 2116 is controlled by a memory controller.

Processor platform 2100 of the illustrated example also includes an interface circuit 2120. Interface circuit 2120 can be implemented by any type of interface standard, such as an Ethernet interface, a universal serial bus (USB), and/or a PCI express interface.

In the illustrated example, one or more input devices 2122 are connected to the interface circuit 2120. Input device(s) 2122 permit(s) a user to enter data and commands into processor 2112. The input device(s) 2122 can be implemented by, for example, an audio sensor, a microphone, a camera (still or video), a keyboard, a button, a mouse, a touchscreen, a track-pad, a trackball, isopoint and/or a voice recognition system.

One or more output devices 2124 are also connected to interface circuit 2120 of the illustrated example. Output devices 2124 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 2120 of the illustrated example, thus, typically includes a graphics driver card, a graphics driver chip or a graphics driver processor.

Interface circuit 2120 of the illustrated example also includes a communication device such as a transmitter, a receiver, a transceiver, a modem and/or network interface card to facilitate exchange of data with external machines (e.g., computing devices of any kind) via a network 2126 (e.g., an Ethernet connection, a digital subscriber line (DSL), a telephone line, coaxial cable, a cellular telephone system, etc.).

Processor platform 2100 of the illustrated example also includes one or more mass storage devices 2128 for storing software and/or data. Examples of such mass storage devices 2128 include floppy disk drives, hard drive disks, compact disk drives, Blu-ray disk drives, RAID systems, and digital versatile disk (DVD) drives.

Coded instructions 2132 associated with any of FIGS. 1-20 can be stored in mass storage device 2128, in volatile memory 2114, in the non-volatile memory 2116, and/or on a removable tangible computer readable storage medium such as a CD or DVD.

It may be noted that operations performed by the processor platform 2100 (e.g., operations corresponding to process flows or methods discussed herein, or aspects thereof) may be sufficiently complex that the operations may not be performed by a human being within a reasonable time period.

CONCLUSION

Thus, certain examples provide a control system to combine information from in-room occupancy sensors (and associated noise-filtering algorithms) with information extracted from (e.g., a hospital and/or other healthcare facility's) medical orders for discharge, transfer and other procedures. The example control system enables automated control and optimization of the timing of inpatient discharge and transfer activity. The example control system enables a hospital to transfer patients to inpatient beds more quickly in order to maximize or otherwise increase the hospital's use of scarce bed capacity and minimize or otherwise reduce admission waiting times experienced by other patients in the hospital system. Certain examples provide automated control of activities associated with readying a hospital inpatient bed to accept a new admission, including scheduling and activation of cleaning staff, so as to optimize or otherwise improve timing of these functions and thereby shorten the time required for bed turnover.

Certain examples provide an automated method to determine an occupancy state of a specific hospital inpatient room, including the bed and surrounding area, which provides a combination of sensitivity and range to reduce or largely eliminate a chance of classifying an occupied room as unoccupied, thereby avoiding unnecessary expense of "false discharge" alerts. The example method does not require any tags or identifiers to be placed upon patients or other individuals and does not require human intervention to enable operations. Multiple instances of the example detection method can be employed to monitor additional rooms simultaneously, and all such instances provide their detection results to a control system. The example detection method includes a level of sensitivity which is sufficient to detect a presence of a patient located in a hospital bed who is sleeping or otherwise inactive under a blanket. The example detection method may involve detection and discrimination of low-level signals such as level of motion due to a patient's respiration (e.g., breathing activity). The example detection method enables protection against false alerts that might otherwise indicate that the patient has been discharged from the room.

Certain examples provide an ability to detect the presence of patients in a larger area in the room beyond the bed, such as those seated in a chair or moving about the room. The example detection method is concerned with detecting the presence or absence of human activity in the specific range outlined by the hospital room, and not with determining the number or identity of individuals.

Certain examples provide an ability to determine the "noise floor" of the room and thereby filter out and eliminate spurious signals of activity, such as from other devices or equipment located in the room. This enables protection against false indications that a patient is currently occupying a room which is actually unoccupied.

Certain examples incorporate and integrate multiple sensing methodologies to implement example detection systems and methods. Example sensing methodologies may include: Doppler radar, thermal imaging, infrared scanning, computer vision, etc. For example, Doppler radar sensor(s) (e.g., a dual Doppler sensor) are to be located out of sight of patients and staff, such as above ceiling tiles, while providing sufficient sensitivity to detect motion due to the respiration of a sleeping patient. Thermal imaging permits detection of human activity within line of sight to the sensor, and can detect a patient sleeping under a blanket. Infrared scanning can detect a moving patient within line of sight to the sensor in a lit or dark room. Computer vision can discriminate the shape or contour of a human from non-human items or equipment and does not require the patient to be in motion.

In a dual Doppler example, the dual Doppler sensor can include a first Doppler sensor with a main antenna lobe pointing downward at a first angle and a second Doppler sensor with a main lobe facing at a second angle (e.g., sideways) different from the first angle. In the example, the first Doppler sensor is to monitor activity (e.g., patient and/or other human activity) in a bed area of the first room, and the second Doppler sensor is to monitor activity (e.g., patient activity, other human activity, robotic activity, etc.) in the first room in a second area larger than the bed area and at least partially beyond a field of view of the first Doppler sensor.

Certain examples provide electrical power and interaction with lights and other environmental controls to provide a variety of capabilities in conjunction with patient and/or room occupancy detection methods. For example, an ability to draw ("siphon") power from existing room lighting and/or low-voltage sources such as smoke/motion detectors. That is, an example sensing system's power is attained without use of dedicated new 120 VAC circuits and associated conduit by adapting to existing power source(s) available in the facility. In certain examples, a management system may include a battery which can power an occupancy sensor when the lights are shut off (e.g., cutting alternating current (A/C) power).

Certain examples provide an ability to provide 'soft control' of room lighting by the occupancy sensor, in which the sensor is constantly powered and lights are turned on by relays controlled by the sensor and/or remote communication from the workflow engine to the sensor. Certain examples provide an ability to provide power conservation functionality by dimming or turning off lights in response to current room occupancy conditions as measured by the invention's occupancy sensor.

Control of the room's temperature and/or humidity levels can be based on a room's current occupancy level, expected future condition(s) as indicated by a workflow engine, etc. For example, a signal may indicate that the room has been assigned to a new patient and is expected to become occupied soon. Therefore, the temperature should be set to the desired level in advance of the patient's arrival.

Certain examples provide an ability to adjust lighting in support clinical protocols involving the room's patient. For example, lighting levels can be used as a notification or warning to a patient who may be attempting to get out of bed in contradiction to a clinical protocol indicating that he or she should remain in the bed.

Such examples cannot be implemented manually by humans and are not merely fundamental practices or methods of organizing human activity. Rather, such examples solve problems in electronic and computer technologies and provide new electronics and computer technology improvements not currently implemented in hospitals or other healthcare facilities (e.g., clinics, doctor's offices, etc.). Examples leverage sensor technology and medical order information to drive workflow and control lighting and/or other environmental systems in rooms based on occupancy information and other gathered data. Multiple components are involved and multiple components are improved and affected, rather than simply organizing data or basic scheduling.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A healthcare workflow management and reasoning system comprising:
   a first processor to monitor one or more medical orders from one or more hospital information systems to identify a condition indicating that a first patient in a first room is ready for discharge; and
   a hardware sensor comprising a second processor and a dual Doppler sensor to gather occupancy data regarding the first patient in the first room and transmit the occupancy data to the first processor,
   wherein the first processor controls one or more hospital operational systems to trigger cleaning of the first room, lighting settings for the first room, transportation of a second patient to the first room, or a combination thereof, based on the occupancy data from the hardware sensor, and wherein the dual Doppler sensor comprises at least a first Doppler sensor with a main antenna lobe pointing in a first direction towards a targeted area in the first room to detect patient activity of the first patient, the targeted area comprising a hospital bed, and a second Doppler sensor with a main lobe positioned in a second direction to detect motion of the first patient outside of the targeted area in the first room, wherein the first Doppler sensor and the second Doppler sensor provide the occupancy data to the first processor.

2. The healthcare workflow management and reasoning system of claim 1, wherein the one or more medical orders include at least one of discharge, transfer, or medical procedure orders for the first patient.

3. The healthcare workflow management and reasoning system of claim 1, wherein the system includes a plurality of hardware sensors, the hardware sensors comprising the dual Doppler sensor and at least one of a thermal imaging sensor, an infrared sensor, or a computer vision sensor.

4. The healthcare workflow management and reasoning system of claim 1, wherein the hardware sensor controls room lighting via one or more relays controlled by the hardware sensor based on communication from the first processor to support execution of a clinical protocol.

5. The healthcare workflow management and reasoning system of claim 1, wherein outside the patient clinical area includes above ceiling tiles of the first room.

6. The healthcare workflow management and reasoning system of claim 1, wherein the first processor is to monitor vital sign data for the first patient from the first Doppler sensor.

7. A computer-implemented method comprising:
monitoring, via a first processor, one or more medical orders from one or more hospital information systems;
identifying, based on the monitored one or more medical orders, a condition indicating that a first patient in a first room is ready for discharge;
gathering, via a hardware sensor comprising a second processor and a dual Doppler sensor, occupancy data regarding the first patient in the first room, wherein the dual Doppler sensor comprises at least a first Doppler sensor and a second Doppler sensor, the first Doppler sensor positioned with a main antenna lobe pointing in a first direction towards a targeted area in the first room to detect patient activity of the first patient, the targeted area comprising a hospital bed, and a second Doppler sensor positioned with a main lobe positioned in a second direction to detect motion of the first patient outside of the targeted area in the first room, wherein the first Doppler sensor and the second Doppler sensor provide the occupancy data to the first processor; and
controlling, via the first processor, one or more hospital operational systems to trigger cleaning of the first room, lighting settings for the first room, transportation of a second patient to the first room based on occupancy data from the hardware sensor, or a combination thereof.

8. The method of claim 7, wherein the one or more medical orders include at least one of discharge, transfer, or medical procedure orders for the first patient.

9. The method of claim 7, further comprising communicating, via the first processor, with a plurality of hardware sensors, the hardware sensors comprising the dual Doppler sensor and at least one of a thermal imaging sensor, an infrared sensor, or a computer vision sensor.

10. The method of claim 7, further comprising controlling, via the hardware sensor, room lighting via one or more relays controlled by the hardware sensor based on communication from the first processor to support execution of a clinical protocol.

11. A non-transitory computer-readable storage medium comprising instructions which, in response to execution by a first processor, configure the first processor to implement a method, the method comprising:
monitoring, via the first processor, one or more medical orders from one or more hospital information systems;
identifying, based on the monitored one or more medical orders, a condition indicating that a first patient in a first room is ready for discharge;
gathering, via a hardware sensor comprising a second processor and a dual Doppler sensor positioned outside a patient clinical area of the first room, occupancy data regarding the first patient in the first room, wherein the dual Doppler sensor comprises at least a first Doppler sensor and a second Doppler sensor, the first Doppler sensor positioned with a main antenna lobe pointing in a first direction towards a targeted area in the first room to detect patient activity of the first patient, the targeted area comprising a hospital bed, and a second Doppler sensor positioned with a main lobe positioned in a second direction to detect motion of the first patient outside of the targeted area in the first room, wherein the first Doppler sensor and the second Doppler sensor provide the occupancy data to the first processor; and
controlling, via the first processor, one or more hospital operational systems to trigger cleaning of the first room, lighting settings for the first room, transportation of a second patient to the first room based on occupancy data from the hardware sensor, or a combination thereof.

12. The computer-readable storage medium of claim 11, wherein the one or more medical orders include at least one of discharge, transfer, or medical procedure orders for the first patient.

13. The computer-readable storage medium of claim 11, wherein the method further comprises communicating, via the first processor, with a plurality of hardware sensors, the hardware sensors comprising the dual Doppler sensor and at least one of a thermal imaging sensor, an infrared sensor, or a computer vision sensor.

14. The computer-readable storage medium of claim 11, wherein the method further comprises controlling, via the hardware sensor, room lighting via one or more relays controlled by the hardware sensor based on communication from the first processor to support execution of a clinical protocol.

15. The computer-readable storage medium of claim 11, wherein the method further comprises determining that the first room is unoccupied by the first patient based on occupancy data from the hardware sensor, an elapsed period of time, and the one or more medical orders related to the first patient.

* * * * *